(12) United States Patent
Wong Chi Man et al.

(10) Patent No.: US 9,896,461 B2
(45) Date of Patent: Feb. 20, 2018

(54) POLYSILYLATED ORGANOSILANE COMPOUNDS

(71) Applicants: CENTRE NATIONAL DE LA RECHERCHE SCIENTIFIQUE (C.N.R.S), Paris (FR); ECOLE NATIONALE SUPERIEURE DE CHIMIE DE MONTPELLIER, Montpellier (FR); UNIVERSITE MONTPELLIER 2, SCIENCES ET TECHNIQUES, Montpellier (FR)

(72) Inventors: Michel Wong Chi Man, Vendargues (FR); Xavier Cattoën, Montpellier (FR); Kristyna Bürglova, Prerov (CZ); Jana Hodacova, Prague (CZ)

(73) Assignees: CENTRE NATIONAL DE LA RECHERCHE SCIENTIFIQUE (C.N.R.S), Paris (FR); ECOLE NATIONALE SUPERIEURE DE CHIMIE DE MONTPELLIER, Montpellier (FR); UNIVERSITE MONTPELLIER, 2 SCIENCES ET TECHNIQUES, Montpellier (FR)

( * ) Notice: Subject to any disclaimer, the term of this patent is extended or adjusted under 35 U.S.C. 154(b) by 302 days.

(21) Appl. No.: 14/412,888

(22) PCT Filed: Jul. 8, 2013

(86) PCT No.: PCT/EP2013/064375
§ 371 (c)(1),
(2) Date: Jan. 5, 2015

(87) PCT Pub. No.: WO2014/006221
PCT Pub. Date: Jan. 9, 2014

(65) Prior Publication Data
US 2015/0218192 A1    Aug. 6, 2015

(30) Foreign Application Priority Data

Jul. 6, 2012 (FR) ..................................... 12 56549

(51) Int. Cl.
C07F 7/18 (2006.01)
C07F 9/40 (2006.01)
C07F 9/6518 (2006.01)

(52) U.S. Cl.
CPC .......... *C07F 7/1836* (2013.01); *C07F 9/4006* (2013.01); *C07F 9/65181* (2013.01)

(58) Field of Classification Search
CPC ... C07F 7/1836; C07F 9/4006; C07F 9/65181
See application file for complete search history.

(56) References Cited

U.S. PATENT DOCUMENTS 6,642,403 B2   11/2003   Arkles et al.
7,235,683 B2    6/2007   Janeiro et al.

OTHER PUBLICATIONS

International Search Report dated Aug. 21, 2013 in PCT/EP2013/064375.
Kristyna Burglova, et al, "Click Approaches to Functional Water-Sensitive Organotriethoxysilanes", Sep. 16, 2011, pp. 7326-7333, vol. 76, No. 18, The Journal of Organic Chemistry.
Moitra, et al., "Convenient route to water-sensitive sol-gel precursors using chemistry", 2010, pp. 8416-8418, vol. 46, Chem. Commun.

*Primary Examiner* — Joseph R Kosack
(74) *Attorney, Agent, or Firm* — B. Aaron Schulman, Esq.; Stites & Harbison, PLLC.

(57) ABSTRACT

The invention concerns a mono- or polyfunctional polysilylated organosilane compound, and the method for preparing same.

9 Claims, No Drawings

POLYSILYLATED ORGANOSILANE COMPOUNDS

The present invention relates to a mono- or poly-functional polysilylated organosilane compound, as well as to its preparation method.

The invention also relates to a functionalized organosilicon material from this compound.

Mono- or poly-functional organosilanes compounds represent a major benefit in many fields, since they allow the making of mono- or poly-functionalized organosilicon materials, which may appear as a powder, a coating or a polymer.

They also allow the making of products which appear as functionalised particles, notably functionalised nanoparticles, for example with an active remainder, which may notably be sorted out in a controlled way under the action of one or several parameters.

Many silylated organosilanes compounds have been described in the prior art (Moitra et al, *Chem. Commun.*, 2010, 46, 8416-8418; Burglova et al, *J. Org. Chem.*, 2011, 76, 7326-7333).

Known compounds are monosilylated, polysilylated compounds where the organic function is a bridging function and comprising simple functionalities such as amine, alcohol, thiol, halide, alkyl derivative, alkylene, phenyl or phenylene functionality.

Documents U.S. Pat. No. 6,642,403 and U.S. Pat. No. 7,235,683 describe monosilylated compounds which may be functionalized.

However, the described compounds only comprise simple functionalities.

Thus, a first object of the invention is to provide mono- or poly-functional polysilylated organosilane compounds which get rid of the problems of the state of the art and which provide a solution to all or part of the problems of the state of the art.

Another object of the invention is to propose mono- or poly-functional polysilylated organosilane compounds, the preparation method of which is easy to apply and with a high yield.

Another object of the invention is to propose polysilylated organosilane compounds allowing the preparation of mono- or poly-functional organosilicon materials which may comprise one or several complex functionalities.

The object of the present invention is a compound of formula (I)

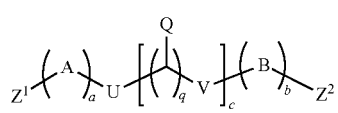

(I)

wherein:
Z$^1$ represents a group of formula

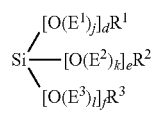

and Z$^2$ represents a group of formula

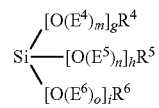

Z$^1$ and Z$^2$ simultaneously represent a group selected from the groups R$^7$R$^8$Si(OH), R$^9$Si(OH)$_2$, Si(OH)$_3$, R$^7$R$^8$SiO$_{1/2}$, R$^9$SiO or SiO$_{3/2}$;

U represents a group selected from the groups of formulae

 (U$^1$)

 (U$^2$)

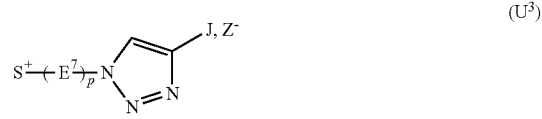 (U$^3$)

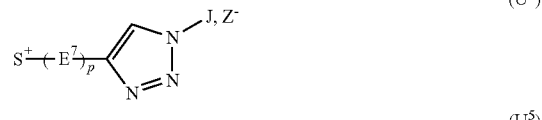 (U$^4$)

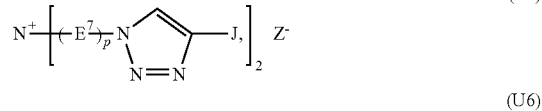 (U$^5$)

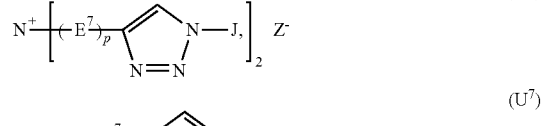 (U$^6$)

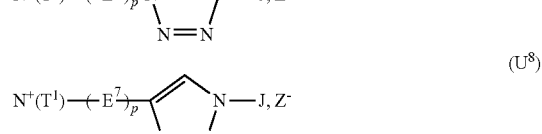 (U$^7$)

 (U$^8$)

R$^1$, R$^2$, R$^3$, R$^4$, R$^5$ and R$^6$, either identical or different, represent a hydrogen atom, a C$_1$-C$_6$-alkyl group, an aryl group, an C$_1$-C$_6$-alkoxy group, a C$_3$-C$_8$-alkylene-alkenyl group;

E$^1$, E$^2$, E$^3$, E$^4$, E$^5$ and E$^6$, either identical or different, represent a C$_1$-C$_6$-alkylene group, C(O), C=CH$_2$ group, an imino-C$_1$-C$_6$-alkyl group, a (C$_1$-C$_6$-alkyl)C=N— group;

d, e, f, g, h, i, either identical or different, represent 0, 1, 2, 3, 4, 5, 6;

j, k, l, m, n, o, either identical or different, represent 0, 1, 2, 3;

R$^7$, R$^8$ and R$^9$, either identical or different, represent a C$_1$-C$_6$-alkyl group, an aryl group, a C$_3$-C$_8$-alkylene-alkenyl group;

A, either identical or different, represents a —CR$^{10}$R$^{11}$ group or a group selected from the groups of formulae

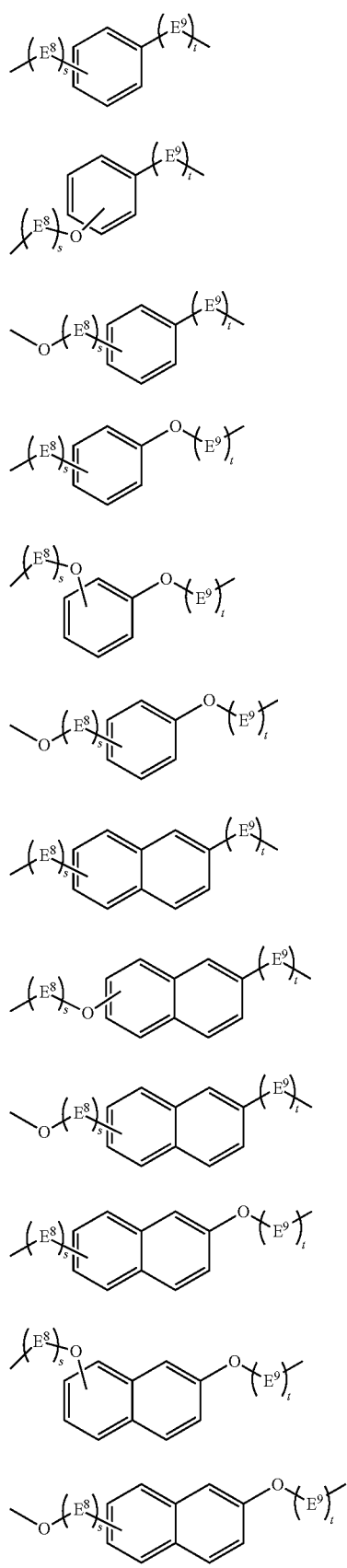
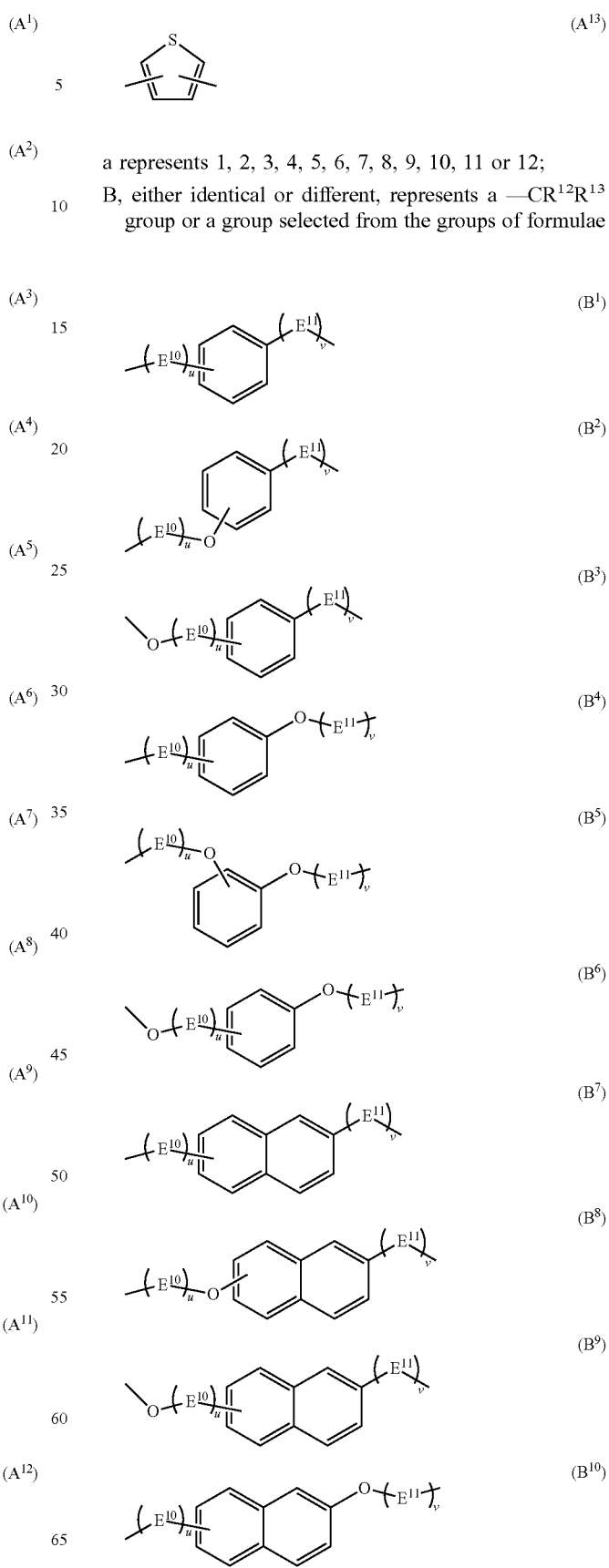
a represents 1, 2, 3, 4, 5, 6, 7, 8, 9, 10, 11 or 12;
B, either identical or different, represents a —$CR^{12}R^{13}$ group or a group selected from the groups of formulae -continued

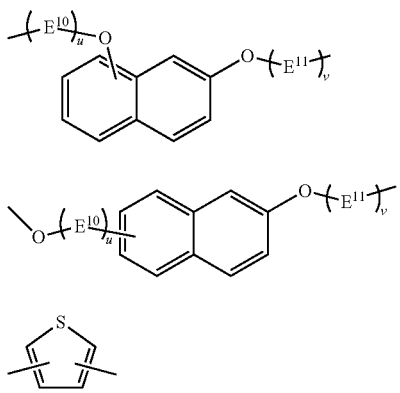

b represents 1, 2, 3, 4, 5, 6, 7, 8, 9, 10, 11 or 12;

V, either identical or different, represents a group selected from the groups of formulae

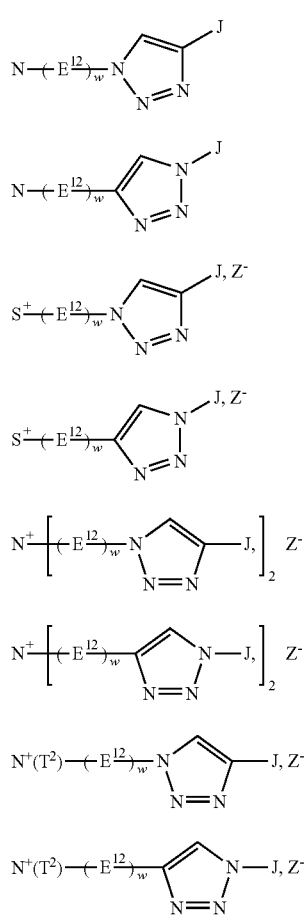

c represents 0, 1, 2 or 3;

Q, either identical or different, represents a hydrogen atom, a $C_1$-$C_{10}$ alkyl group, a $C_1$-$C_{10}$ alkoxy group, a $C_3$-$C_{10}$ cycloalkyl group, an aryl group; at least 2 Q groups and the carbon atoms to which they are bound form a carbocycle with 5, 6, 7, 8, 9 or 10 carbon atoms, substituted or non-substituted, either aromatic or non-aromatic, saturated, partly or totally unsaturated, fused or non-fused;

q represents 0, 1, 2, 3, 4, 5, 6, 7, 8, 9, 10, 11 or 12;

$E^7$, $E^8$, $E^9$, $E^{10}$, $E^{11}$ and $E^{12}$ either identical or different, represent a group $CR^{14}R^{15}$, a group $OCR^{16}R^{17}$;

s, t, u and v, either identical or different, represent 0, 1, 2, 3, 4, 5, 6;

$T^1$ and $T^2$, either identical or different, represents a group $(E^{13})_x Si(R^{18})(R^{19})(R^{20})$;

$E^{13}$ represents a group —$CR^{21}R^{22}$;

$R^{10}$, $R^{11}$, $R^{12}$, $R^{13}$, $R^{14}$, $R^{15}$, $R^{16}$, $R^{17}$, $R^{18}$, $R^{19}$, $R^{20}$, $R^{21}$ and $R^{22}$, either identical or different, represent a hydrogen atom, a $C_1$-$C_6$-alkyl group, a $C_1$-$C_6$-alkoxy group, a $C_3$-$C_8$-alkylene-alkenyl group, an aryl group, an aryloxy group;

J represents an atom or a terminal group, an atom or a divalent, trivalent, tetravalent, pentavalent or hexavalent group, either mono- or polyfunctional;

p, w and x either identical or different, represent 1, 2, 3, 4, 5, 6, 7, 8, 9, 10, 11 or 12;

$Z^-$ represents an anion selected from halides, $BF_4^-$, $B(Ph)_4^-$, $CO_3^{2-}$, $R^{23}CO_2^-$, $R^{24}SO_3^-$, $SO_4^{2-}$, $PO_4^{3-}$, $HPO_3^{2-}$, $NO_3^-$;

$R^{23}$ represents a $C_1$-$C_3$ alkyl group or an aryl group;

$R^{24}$ represents a $C_1$-$C_3$ alkyl group, an aryl group or a group —$CF_3$;

as well as an enantiomer, an isomer or a diastereoisomer of this compound.

According to the invention, in the groups of formulae $A^7$ to $A^{12}$ and $B^7$ to $B^{12}$, the substituting groups may be present on one of the aryl groups forming the naphthyl remainder or on each of the aryl groups forming the naphthyl remainder.

According to the invention, in the groups $U^1$, $U^2$, $U^5$, $U^6$, $U^7$, $U^8$, $V^1$, $V^2$, $V^5$, $V^6$, $V^7$ and $V^8$, the nitrogen atom ensures the binding with the remainder of the compound of formula (I).

According to the invention, in the groups $U^3$, $U^4$, $U^5$, $V^3$ and $V^4$, the sulphur atom ensures the binding with the remainder of the compound of formula (I).

The compound according to the invention may be a compound of formula (II)

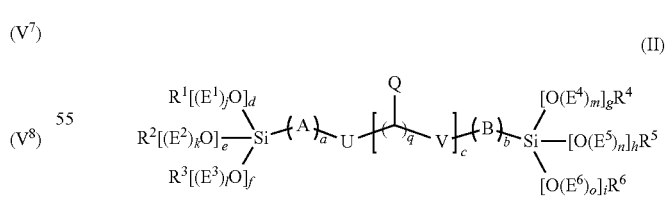

The definitions of $R^1$, $R^2$, $R^3$, $R^4$, $R^5$, $R^6$, $E^1$, $E^2$, $E^3$, $E^4$, $E^5$, $E^6$, A, U, Q, V, B, a, b, c, d, e, f, g, h, i, j, k, l, m, n, o and q for the compound of formula (I) according to the invention are applied to the compound of formula (II) according to the invention.

The invention also provides a compound of formula (IIa) or (IIb)

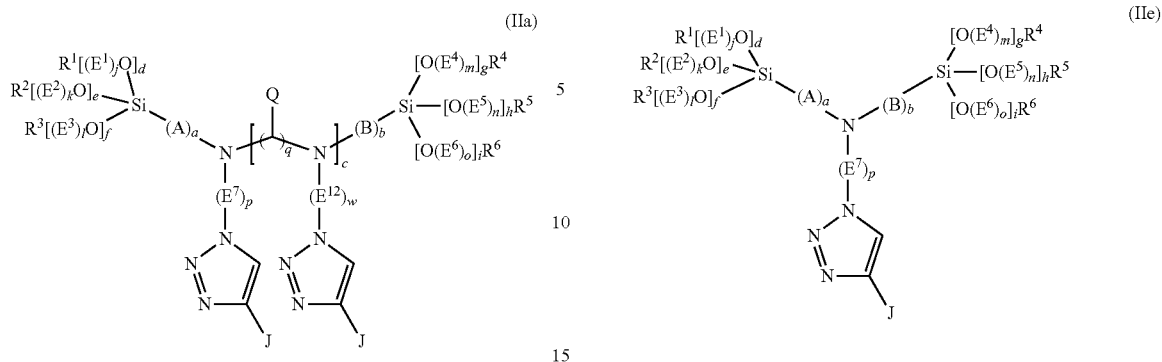

(IIa)

(IIb)

The definitions of $R^1$, $R^2$, $R^3$, $R^4$, $R^5$, $R^6$, $E^1$, $E^2$, $E^3$, $E^4$, $E^5$, $E^6$, $E^7$, $E^{12}$, A, B, Q, a, b, c, d, e, f, g, h, i, j, k, l, m, n, o, p, q, w and J for the compound of formula (I) according to the invention apply to the compounds of formula (IIa) and (IIb) according to the invention.

The invention also provides a compound of formula (IIc) or (IId)

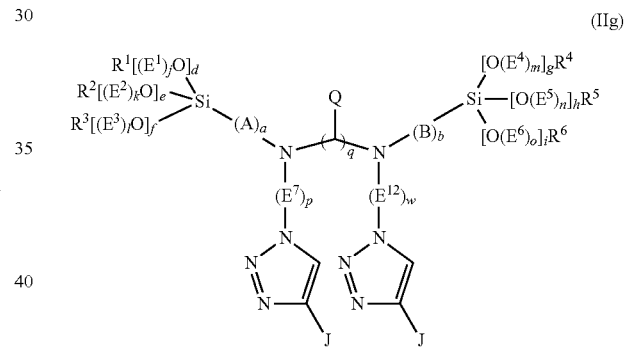

(IIc)

(IId)

The definitions of $R^1$, $R^2$, $R^3$, $R^4$, $R^5$, $R^6$, $E^1$, $E^2$, $E^3$, $E^4$, $E^5$, $E^6$, A, U, Q, V, B, a, b, d, e, f, g, h, i, j, k, l, m, n, o and q for the compound of formula (I) according to the invention applied to the compounds of formula (IIc) and (IId) according to the invention.

The invention also provides a compound of formulae (IIe), (IIf), (IIg) or (IIh)

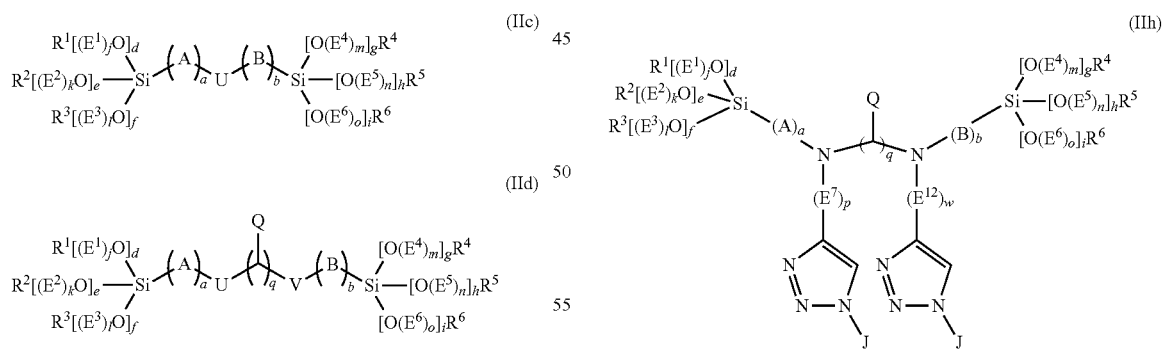

(IIe)

(IIf)

(IIg)

(IIh)

The definitions of $R^1$, $R^2$, $R^3$, $R^4$, $R^5$, $R^6$, $E^1$, $E^2$, $E^3$, $E^4$, $E^5$, $E^6$, $E^7$, $E^{12}$, A, B, Q, a, b, d, e, f, g, h, i, j, k, l, m, n, o, p, q, w and J for the compound of formula (I) according to the invention applied to the compounds of formulae (IIe), (IIf), (IIg) and (IIh) according to the invention.

The invention also provides a compound of formulae (III) to (VIII)

(III)

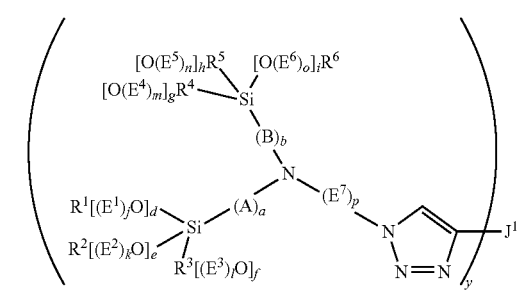

(IV)

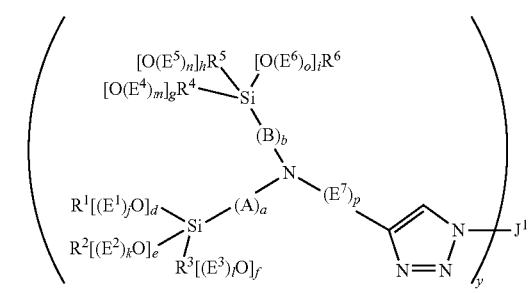

(V)

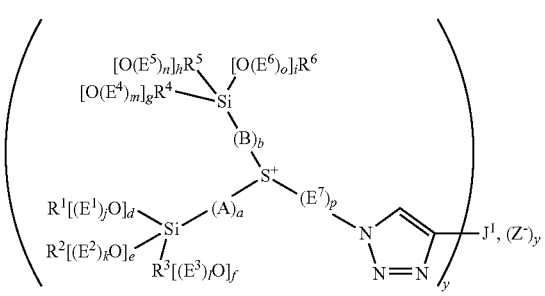

(VI)

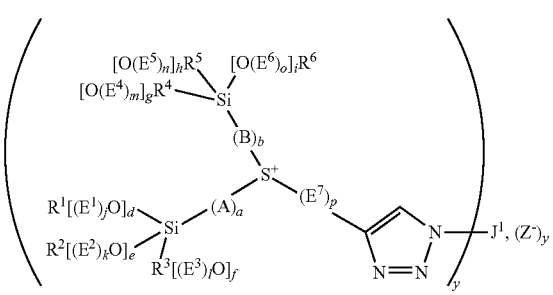

(VII)

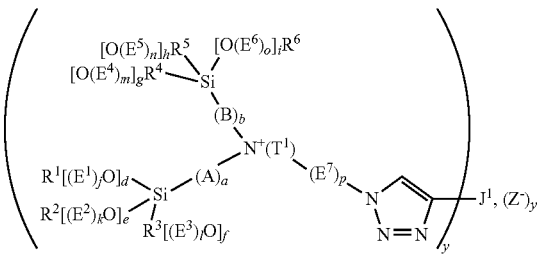

(VIII)

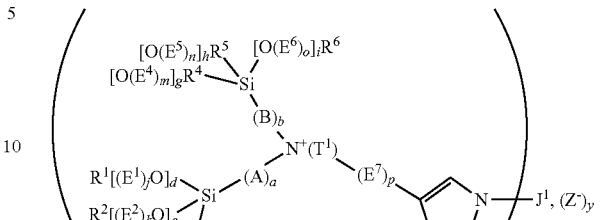

For the compounds of formulae (III) to (VIII) according to the invention:

$R^1$, $R^2$, $R^3$, $R^4$, $R^5$ and $R^6$, either identical or different, may independently represent a hydrogen atom, a $C_1$-$C_6$-alkyl group, an aryl group, a u $C_1$-$C_6$-alkoxy group, a $C_3$-$C_8$-alkylene-alkenyl group;

$E^1$, $E^2$, $E^3$, $E^4$, $E^5$ and $E^6$, either identical or different, may independently represent a $C_1$-$C_6$-alkylene group, C(O), C=$CH_2$ group, an imino-$C_1$-$C_6$-alkyl group, a ($C_1$-$C_6$-alkyl)C=N— group;

$J^1$ may represent an atom or a divalent, trivalent, tetravalent, pentavalent or hexavalent, mono- or polyfunctional group;

y may represent 2, 3, 4, 5 or 6.

The definitions of $E^7$, A, B, a, b, d, e, f, g, h, i, j, k, l, m, n, o, p and Z for the compound of formula (I) according to the invention apply to the compounds of the formulae (III) to (VIII) according to the invention.

The invention also provides a compound of formulae (IIIa) or (IVa)

(IIIa)

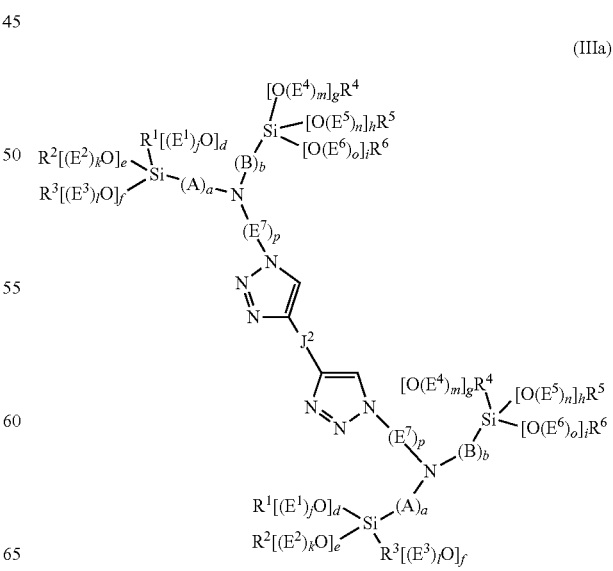

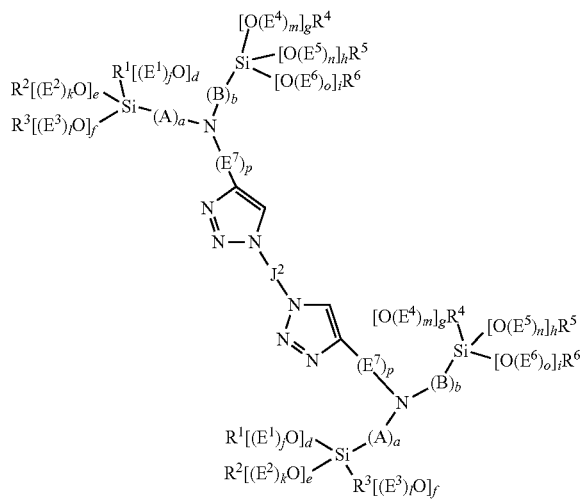

For the compounds of formulae (IIIa) and (IVa) according to the invention:

$R^1$, $R^2$, $R^3$, $R^4$, $R^5$ and $R^6$, either identical or different, may independently represent a hydrogen atom, a $C_1$-$C_6$-alkyl group, an aryl group, a $C_1$-$C_6$-alkoxy group, a $C_3$-$C_8$-alkylene-alkenyl group;

$E^1$, $E^2$, $E^3$, $E^4$, $E^5$ and $E^6$, either identical or different, may independently represent a $C_1$-$C_6$-alkylene group, C(O), C=CH$_2$, an imino-$C_1$-$C_6$-alkyl group, a group ($C_1$-$C_6$-alkyl)C=N—;

$J^2$ represents an atom or a divalent, mono- or polyfunctional group;

The definitions of $E^7$, A, B, a, b, d, e, f, g, h, i, j, k, l, m, n, o and p for the compound of formula (I) according to the invention apply to the compounds of formulae (IIIa) and (IVa) according to the invention.

The invention also provides a compound of formulae (IIIb) or (IVb)

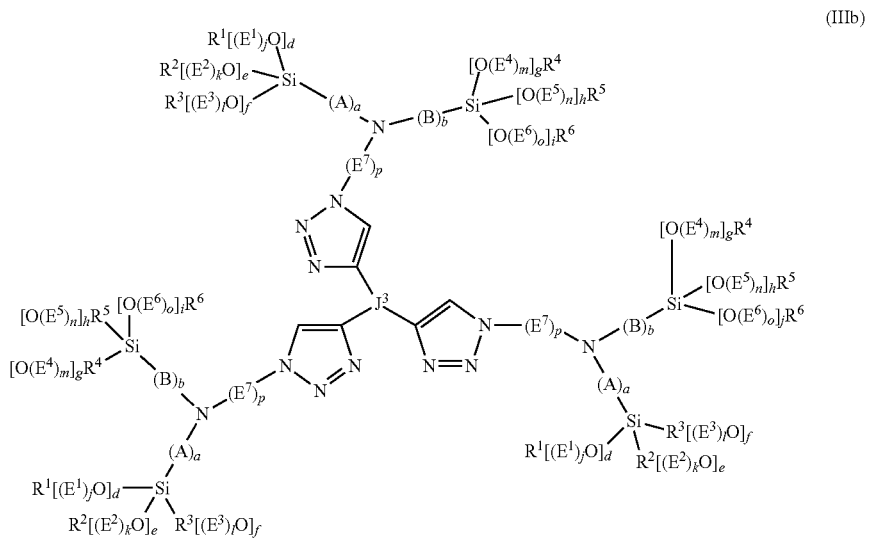

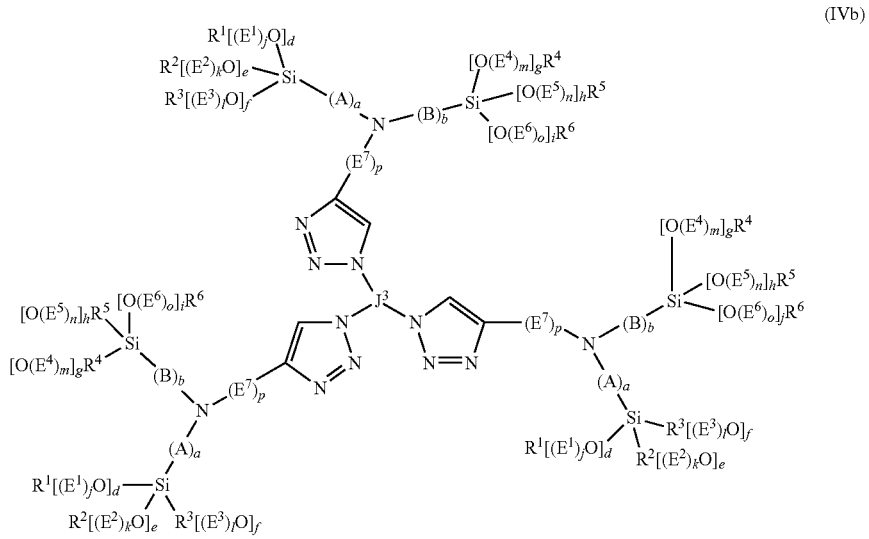

For the compounds of formulae (IIIb) and (IVb) according to the invention:

$R^1$, $R^2$, $R^3$, $R^4$, $R^5$ and $R^6$, either identical or different, may independently represent a hydrogen atom, a $C_1$-$C_6$-alkyl group, an aryl group, a $C_1$-$C_6$-alkoxy group, a $C_3$-$C_8$-alkylene-alkenyl group;

$E^1$, $E^2$, $E^3$, $E^4$, $E^5$ and $E^6$, either identical or different, may independently represent a $C_1$-$C_6$-alkylene group, C(O), C=$CH_2$ group, an imino-$C_1$-$C_6$-alkyl group, a group ($C_1$-$C_6$-alkyl)C=N—;

$J^3$ represents an atom or a trivalent, mono- or polyfunctional group.

The definitions of $E^7$, A, B, a, b, d, e, f, g, h, i, j, k, l, m, n, o and p for the compound of formula (I) according to the invention applied to the compounds of formulae (IIIb) and (IVb) according to the invention.

The invention also provides a compound of formulae (IIIc) or (IVc)

For the compounds of formulae (IIIc) and (IVc) according to the invention:

$R^1$, $R^2$, $R^3$, $R^4$, $R^5$ and $R^6$, either identical or different, may independently represent a hydrogen atom, a $C_1$-$C_6$-alkyl group, an aryl group, a $C_1$-$C_6$-alkoxy group, a $C_3$-$C_8$-alkylene-alkenyl group;

$E^1$, $E^2$, $E^3$, $E^4$, $E^5$ and $E^6$, either identical or different, may independently represent a $C_1$-$C_6$-alkylene group, C(O), C=$CH_2$ group, an imino-$C_1$-$C_6$-alkyl group, a group ($C_1$-$C_6$-alkyle)C=N—;

$J^4$ represents an atom or a tetravalent, mono- or polyfunctional group.

The definitions of $E^7$, A, B, a, b, d, e, f, g, h, i, j, k, l, m, n, o and p for the compound of formula (I) according to the invention apply to the compounds of formulae (IIIc) and (IVc) according to the invention.

The invention also provides a compound of formulae (IX), (X) or (XI)

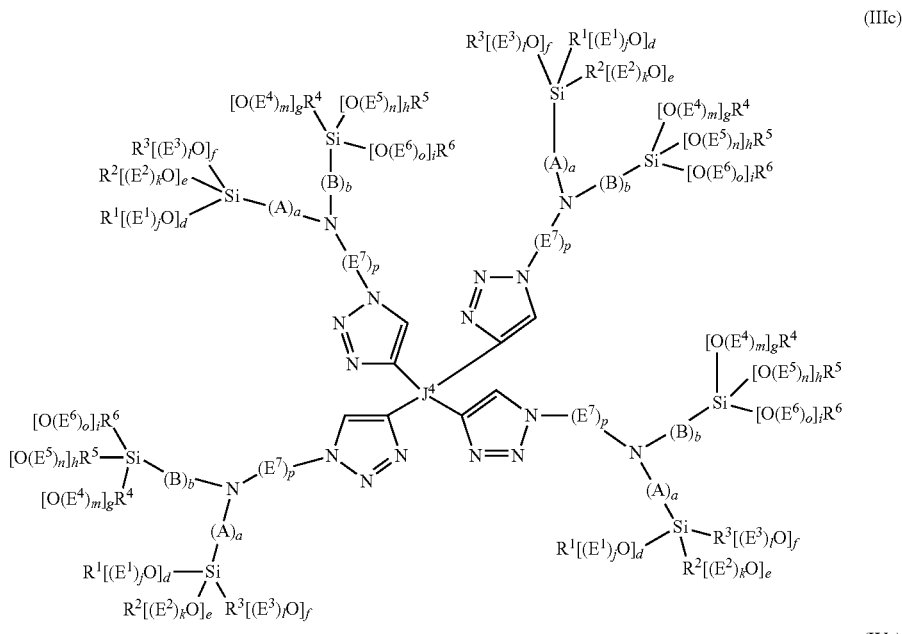

(IIIc)

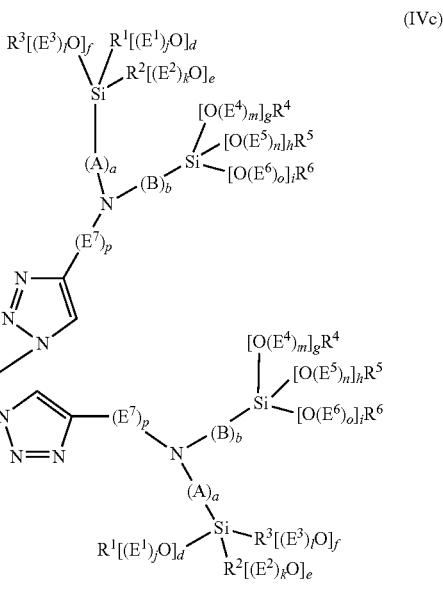

(IVc)

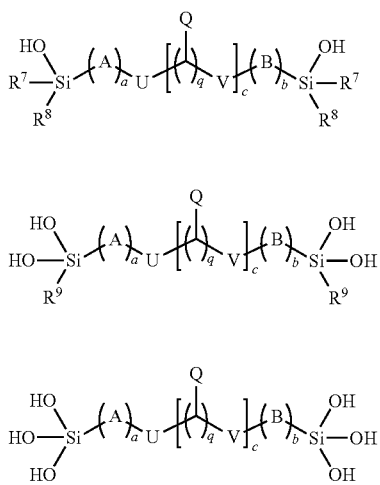

(IX)

(X)

(XI)

The definitions of $R^7$, $R^8$, $R^9$, A, U, Q, V, B, a, b, c and q for the compound of formula (I) according to the invention apply to the compounds of formulae (IX), (X) and (XI) according to the invention.

The invention also provides a compound of formula (XII), (XIII) or (XIV), obtained by polycondensation of a compound of formula (IX), (X) or (XI), respectively.

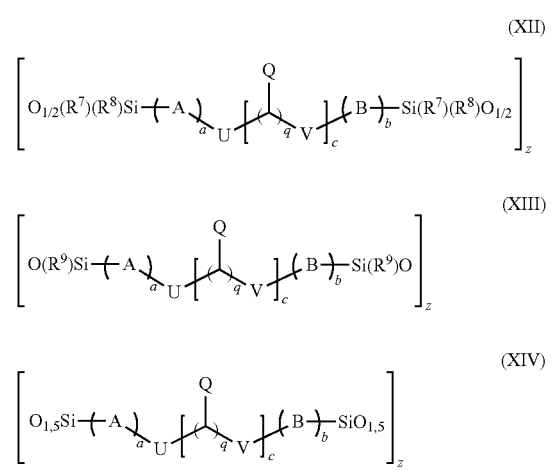

(XII)

(XIII)

(XIV)

For the compounds of formulae (XII), (XIII) and (XIV) according to the invention, z may represent an integer ranging from 2 to 2,000,000.

The definitions of $R^7$, $R^8$, $R^9$, A, U, Q, V, B, a, b, c and q for the compound of formula (I) according to the invention apply to the compounds of formulae (XII), (XIII) and (XIV) according to the invention.

According to the invention, the formulae (XII), (XIII) or (XIV) are units present within polymeric structures. Thus, the compounds of formulae (XII), (XIII) or (XIV) represent monomers or oligomers for preparing other oligomers or polymers.

The invention provides an example of a compound of formula (XIV):

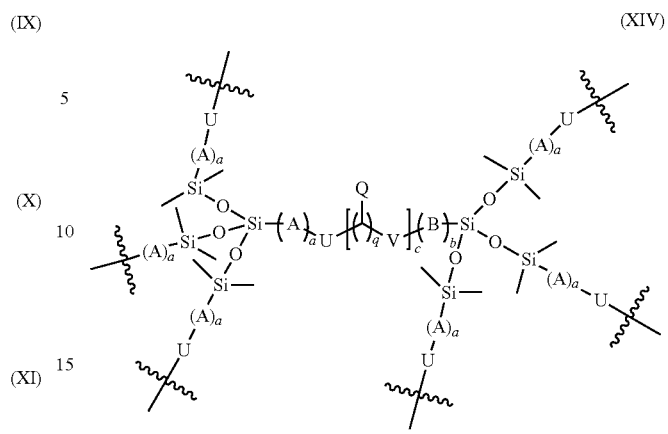

(XIV)

The definitions of A, U, Q, V, B, a, b, c and q for the compound of formula (I) apply to compounds of formula (XIV).

Advantageously, for the compounds according to the invention:
A and B represent a group —(CH$_2$)—; or
Q represents a hydrogen atom; or
$R^1$, $R^2$, $R^3$, $R^4$, $R^5$ and $R^6$ independently represent a group Me or Et; or
a represents 1, 2 or 3; or
b represents 1, 2 or 3; or
q represents 0, 1, 2, 3 or 4; or
d, e, f, g, h and i, either identical or different, represent 0 or 1; or
j, k, l, m, n and o represent 0; or
$R^7$ represents a group methyl, ethyl or phenyl; or
$R^8$ represents a methyl, ethyl or phenyl group; or
$R^9$ represents a methyl, ethyl or phenyl group; or
$R^{28}$ represents a methyl group or a phenyl group; or
$R^{29}$ represents a methyl group, a phenyl group or a group —CF$_3$.

Advantageously, the compound according to the invention is a compound of formulae (II), (IIa), (IIb), (IIc), (IId), (IIe), (IIf), (IIg), (IIh), (III), (IV), (V), (VI), (VII) or (VIII) wherein:
A and B represent a group —(CH$_2$)—;
Q represents a hydrogen atom;
$R^1$, $R^2$, $R^3$, $R^4$, $R^5$ and $R^6$ independently represent a group Me or Et;
a represents 1, 2 or 3;
b represents 1, 2 or 3;
q represents 0, 1, 2, 3 or 4;
d, e, f, g, h and i, either identical or different, represent 0 or 1;
j, k, l, m, n and o represent 0;
$R^{28}$ represents a methyl group or a phenyl group; or
$R^{29}$ represents a methyl group, a phenyl group or a group —CF$_3$.

Also advantageously, the compound according to the invention is a compound of formulae (II), (IIa), (IIb), (IIc), (IId), (IIe), (IIf), (IIg), (IIh), (III), (IV), (V), (VI), (VII) or (VIII) wherein $R^1$, $R^2$, $R^3$, $R^4$, $R^5$ and $R^6$ independently represent an alkoxy group, preferably methoxy or ethoxy.

Advantageously, when $R^1$, $R^2$, $R^3$, $R^4$, $R^5$ and $R^6$ independently represent an alkoxy group, j, k, l, m, n and o do not represent 0.

Advantageously, the compound according to the invention is a compound of formulae (IX), (X), (XI), (XII), (XII) or (XIV) wherein:

A and B represent a group —(CH$_2$)—;
Q represents a hydrogen atom;
a represents 1, 2 or 3;
b represents 1, 2 or 3;
q represents 0, 1, 2, 3 or 4;
R$^7$ represents a methyl, ethyl or phenyl group;
R$^8$ represents a methyl, ethyl or phenyl group;
R$^9$ represents a methyl, ethyl or phenyl group.

According to the invention, J, J$^1$, J$^2$, J$^3$ and J$^4$ may independently represent a mono- or poly-functional group comprising at least one functional group selected from a colouring group, a catalyst group, a group allowing molecular recognition, a biologically active group, a redox group, a hydrophilic group, a hydrophobic group, a decontaminating complexing group, a catalyst complexing group, a cross-linking group or a structuring group.

According to the invention, the functional group may be selected from:
- a colouring group selected from an azoic, triphenylmethane, phthalein, a quinonic, a indigoid, an azinic, a porphyrin, a phthalocyanin, boron-dipyromethene, a naphthalimide, a polyaromatic, a pyrene, acridin, and derivatives thereof, a colouring agent comprising a conjugate π system, a fluorescent colouring agent or a phosphorescent colouring agent;
- a catalyst group selected from a proline, a prolinamide, a diaryl-prolinol, 1,1'-bis-2-naphthol, trans-1,2-diaminocyclohexane, tartaric acid, 1,2-diphenylethylenediamine, bisoxazoline, phosphine-oxazoline, pyridine-bisoxazoline, triarylphosphine, diphosphine, an imidazolium salt, a N-heterocyclic metal-carbene complex, a bipyridine, a pyridine, a phenanthroline, cyclopentadiene and derivatives thereof;
- a group allowing molecular recognition selected from a nitrogen-containing base, a melamin and derivatives thereof;
- a redox group selected from a metallocene, 1,4-(4-aminophenyl)-butadiene, a fullerene, a carbon nanotube and derivatives thereof;
- a hydrophobic group selected from a C$_1$-C$_{30}$ alkyl group, non-substituted or substituted with at least one fluorine atom, an aryl group;
- a decontaminating complexing group selected from an amine, an alcohol, a pyridine, a bipyridine, a triarylphosphine, a malonamide, a diacid, a diketone and derivatives thereof;
- a catalyst complexing group selected from a proline, a diarylprolinol and derivatives thereof;
- a crosslinking group selected from butadiene, butadiyne, an acrylate, a methacrylate, vinyl, styryl and derivatives thereof,
- a structuring group selected from a pyrrole, thiophene, alkylene or phenylene.

According to the invention, J may represent a mono- or poly-functional group comprising at least one functional group selected from:
- a colouring group selected from boron-dipyromethene, naphthalimide, a porphyrin, a phthalocyanine, an azoic, an indigoid, a phthalein, a quinonic and derivatives thereof;
- a decontaminating complexing group selected from an amine, an alcohol, a pyridine, a triarylphosphine, a malonamide, a diacid, a diketone and derivatives thereof;
- a group allowing molecular recognition selected from a nitrogen-containing base, a melamin and derivatives thereof;
- a catalyst complexing group selected from a proline, a diarylprolinol and derivatives thereof;
- a redox group selected from a metallocene;
- a hydrophobic group selected from a C$_1$-C$_{30}$ alkyl group, non-substituted or substituted with at least one fluorine atom;
- a structuring group selected from a pyrrole or a thiophene.

Advantageously, J represents a group of formulae (J-1) to (J-46)

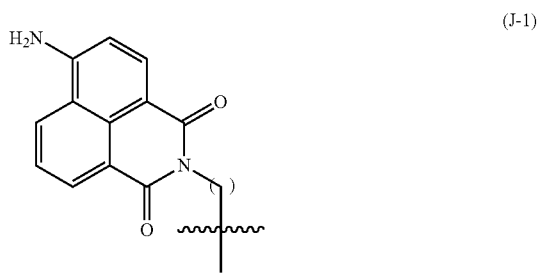
(J-1)

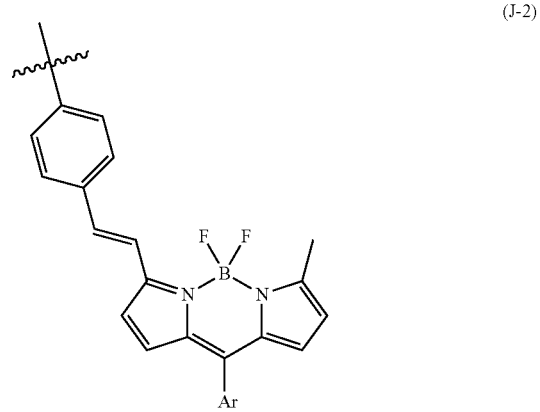
(J-2)

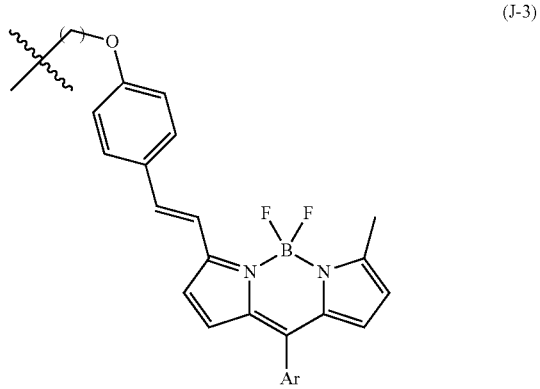
(J-3)

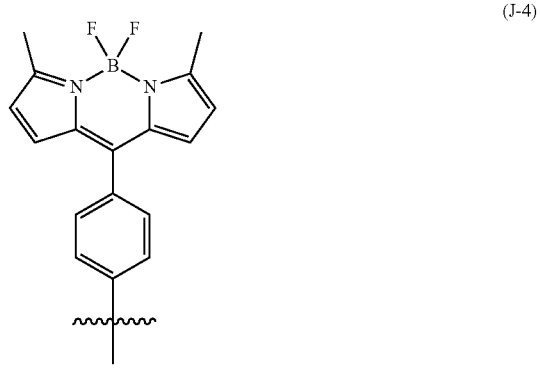
(J-4)

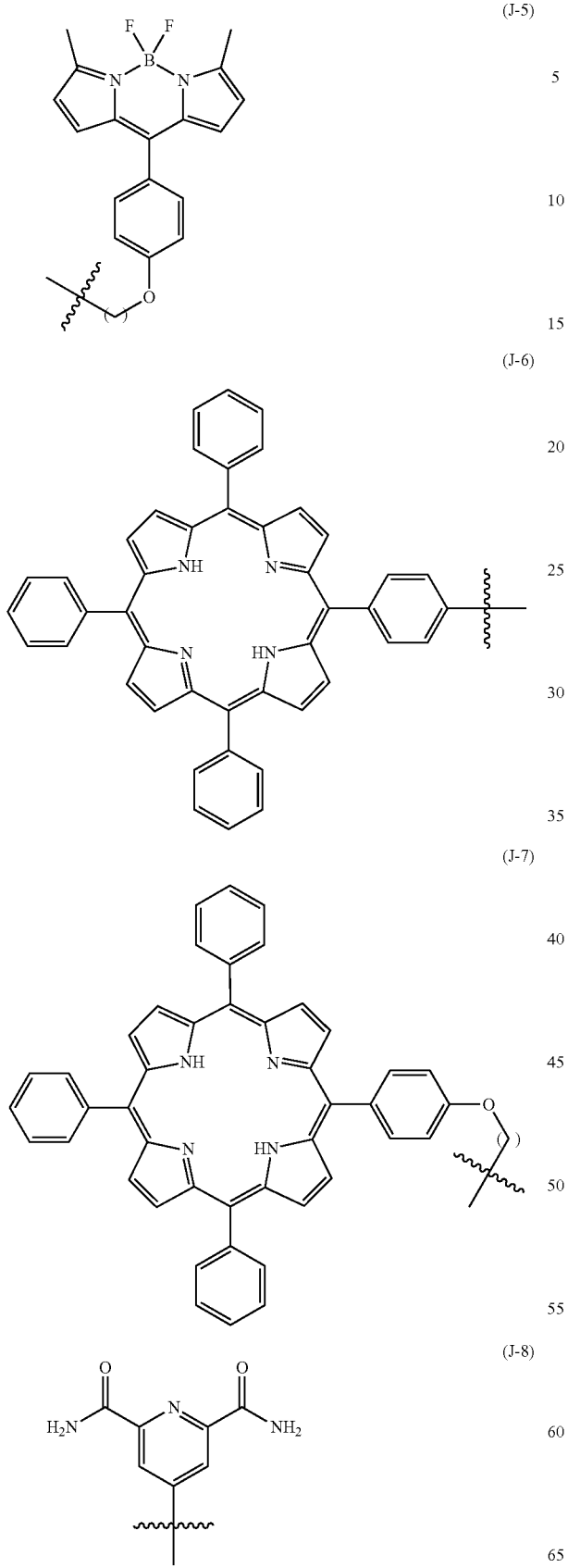

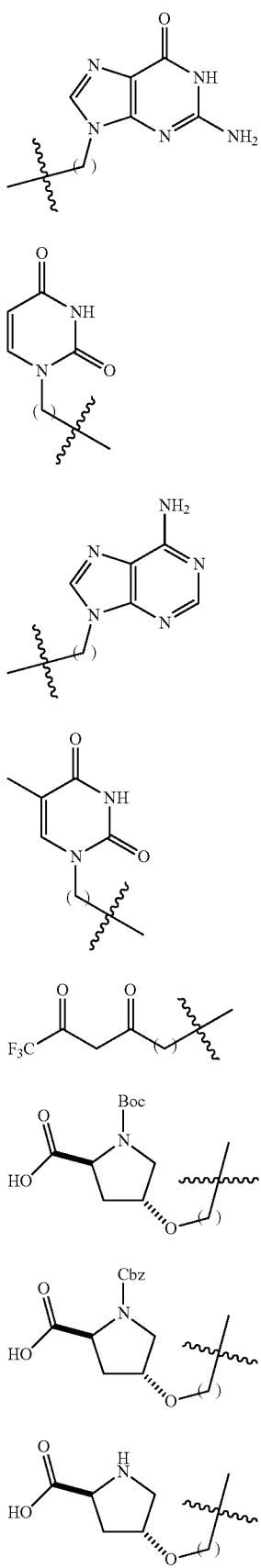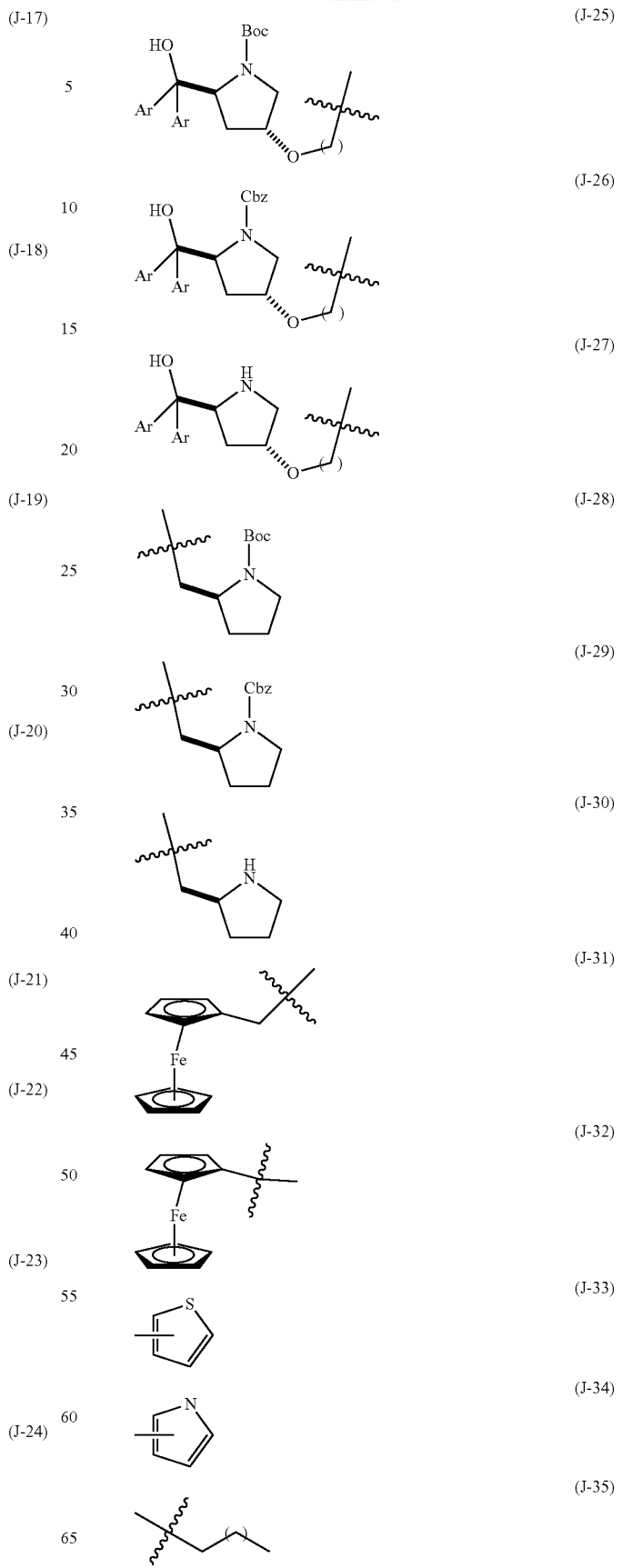

(J-36)
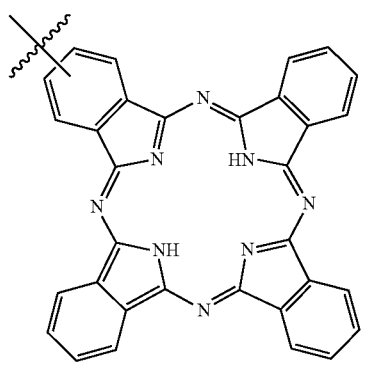
(J-37)
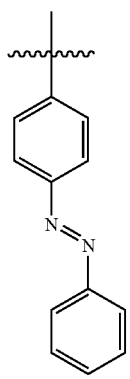
(J-38)
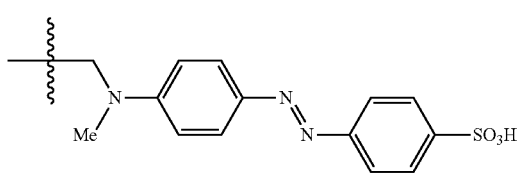
(J-39)
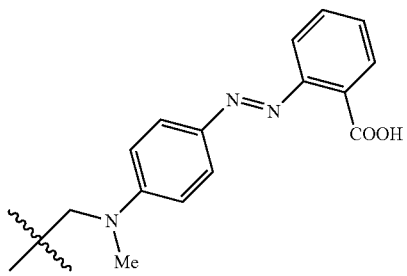
(J-40)
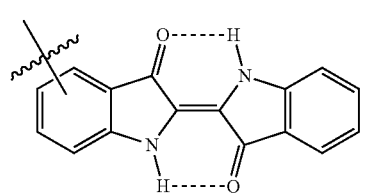
(J-41)
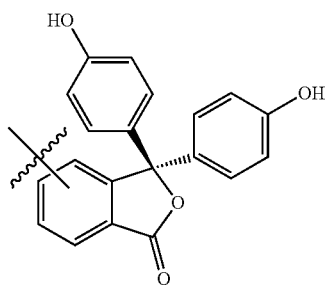
(J-42)
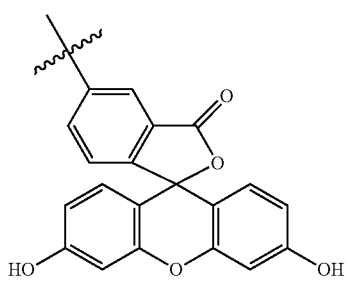
(J-43)
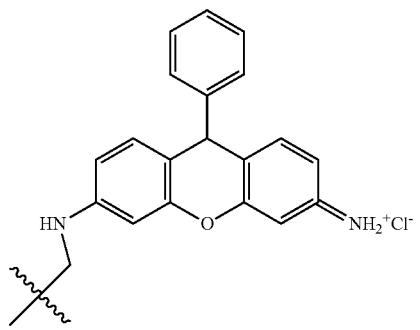
(J-44)
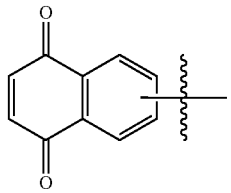
(J-45)
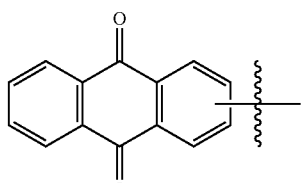
(J-46)
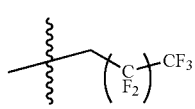
By Cbz, is meant a carboxybenzyl group.
By Boc, is meant a tert-butoxycarbonyl group.
Advantageously, for the groups of formulae (J-1), (J-3), (J-5), (J-7), (J-10), (J-12), (J-14), (J-15), (J-16), (J-17), (J-18), (J-19), (J-20), (J-21), (J-22), (J-23), (J-24), (J-25), (J-26), (J-27) and (J-35), the binding with the triazole group is accomplished with an alkylene chain comprising from 0 to 15, preferably from 0 to 12 units —(CH$_2$)—.

Advantageously, for the group of formulae (J-46), the number of units —CF$_2$— ranges from 4 to 18.

According to the invention, J$^2$ may represent a mono- or poly-functional group comprising at least one functional group selected from:

- a colouring group selected from boron-dipyromethene, a porphyrin, a phthalocyanin, an azoic, an indigoid, a phthalein, a quinonic, a triphenylmethane, a colouring agent comprising at least one conjugate π system, a pyrene and derivatives thereof;
- a decontaminating complexing group selected from a pyridine, a bipyridine, a triarylphosphine, a malonamide, a diketone and derivatives thereof;
- a group allowing molecular recognition selected from a melamin and derivatives thereof;
- a catalyst group selected from a binol, a derivative of 2,2'-bis(diphenylphosphino)-1,1'-binaphthyl (BINAP), a derivative of 2,2'-diamino-1,1'-binaphthyl (BINAM), trans-1,2-diaminocyclohexane, 1,2-diphenylethylene-1,2-diamine, tartaric acid and derivatives thereof;
- a redox group selected from 1,4-(4-aminophenyl)-butadiene, a metallocene and derivatives thereof;
- a hydrophobic group selected from a C$_1$-C$_{30}$ alkyl group, non-substituted or substituted with at least one fluorine atom, an aryl group;
- a structuring group selected from a thiophene, an alkylene.

Advantageously, J$^2$ represents a group of formulae (J$^2$-1) to (J$^2$-48)

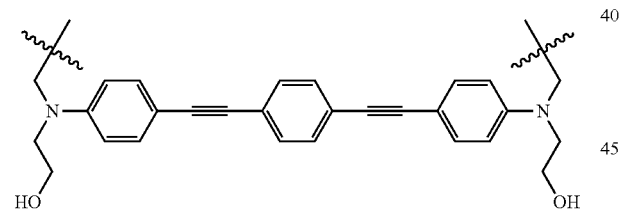
(J$^2$-1)

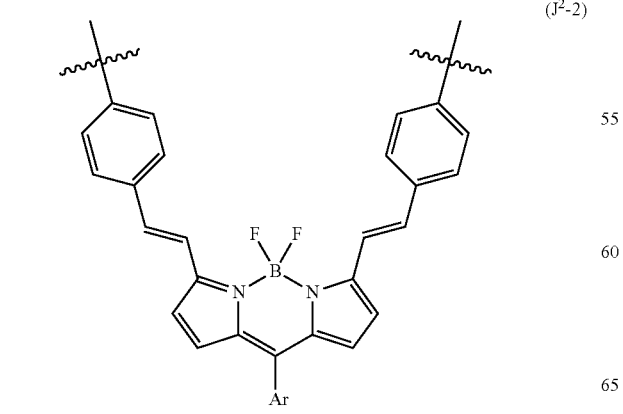
(J$^2$-2)

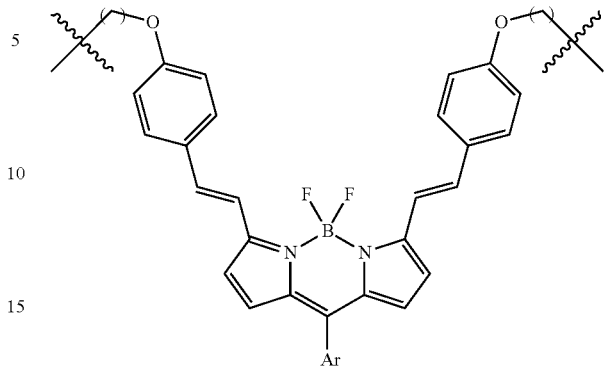
(J$^2$-3)

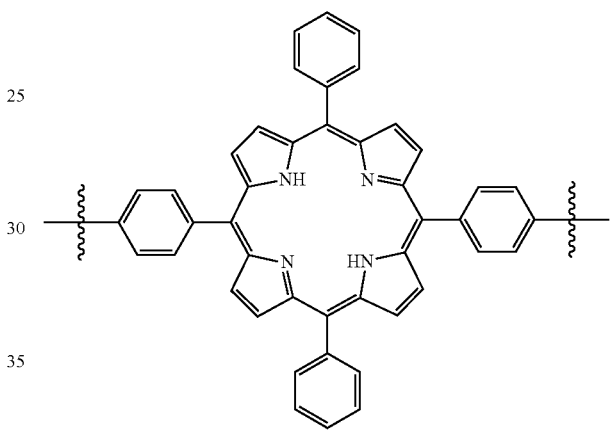
(J$^2$-4)

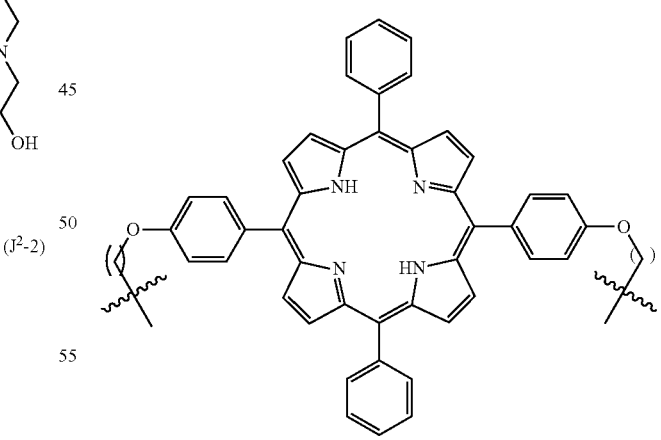
(J$^2$-5)

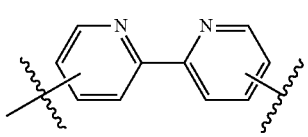
(J$^2$-6)

(J²-7)
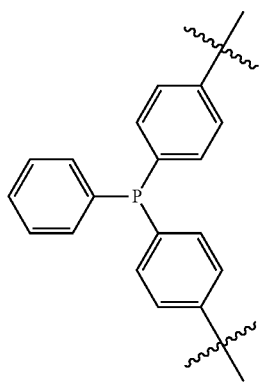
(J²-8)
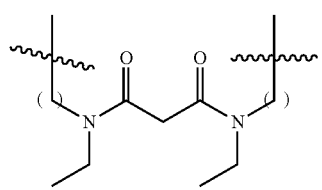
(J²-9)
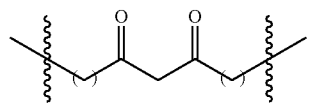
(J²-10)
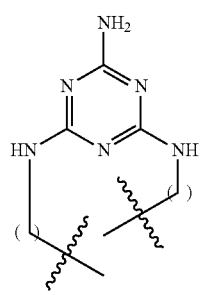
(J²-11)
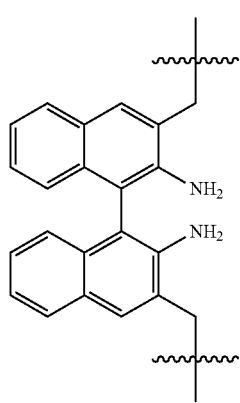
(J²-12)
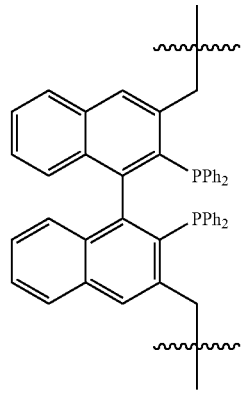
(J²-13)
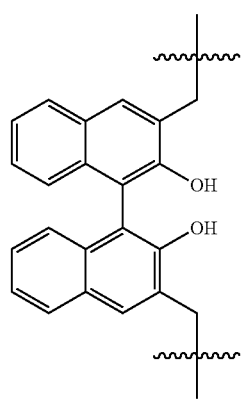
(J²-14)
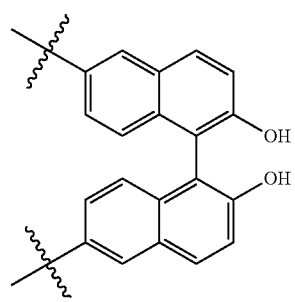
(J²-15)
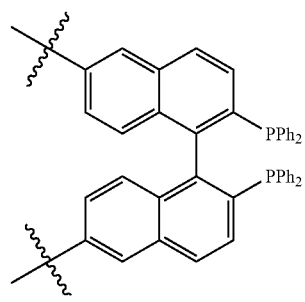

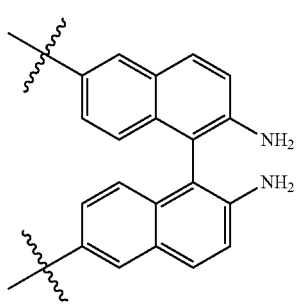 (J²-16)
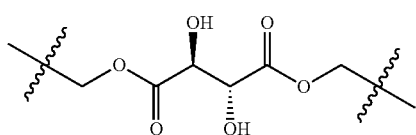 (J²-17)
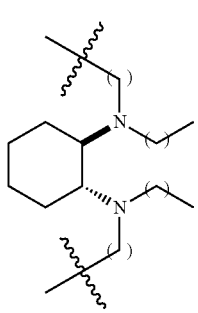 (J²-18)
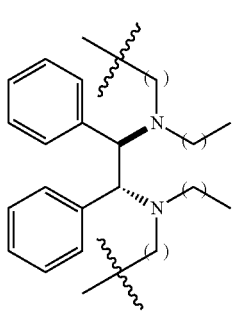 (J²-19)
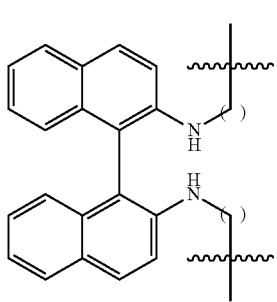 (J²-20)
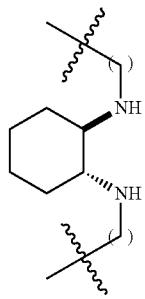 (J²-21)
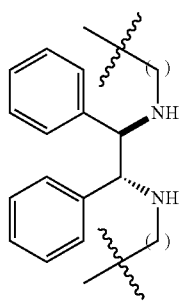 (J²-22)
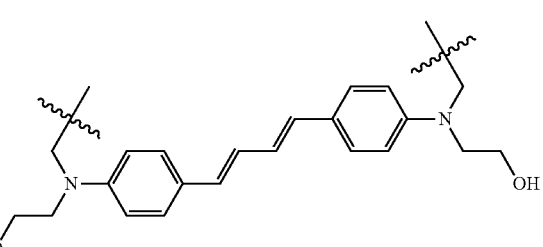 (J²-23)
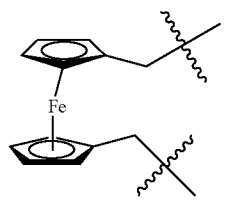 (J²-24)
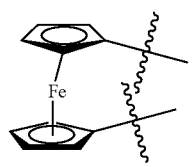 (J²-25)
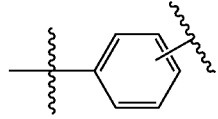 (J²-26)
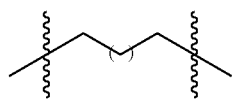 (J²-27)

-continued
(J²-28)
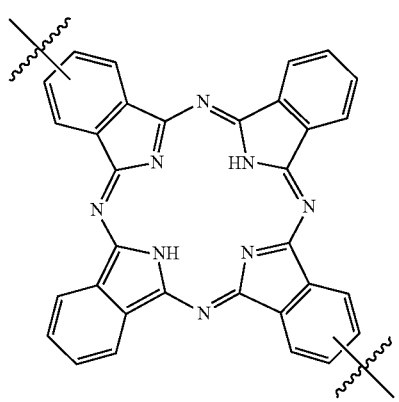
(J²-29)
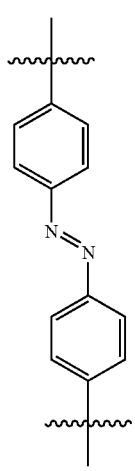
(J²-30)
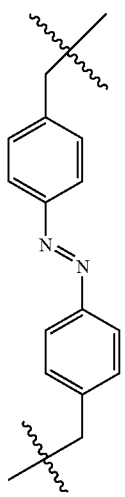
(J²-31)
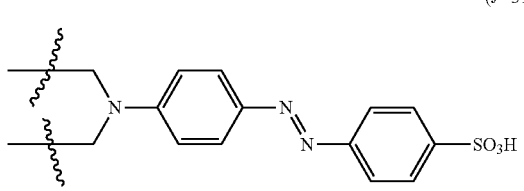
-continued
(J²-32)
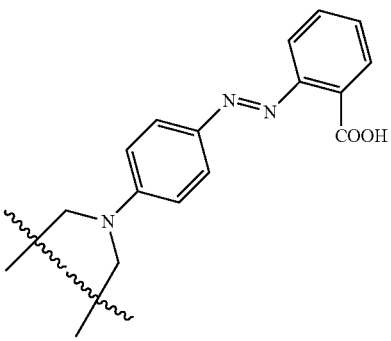
(J²-33)
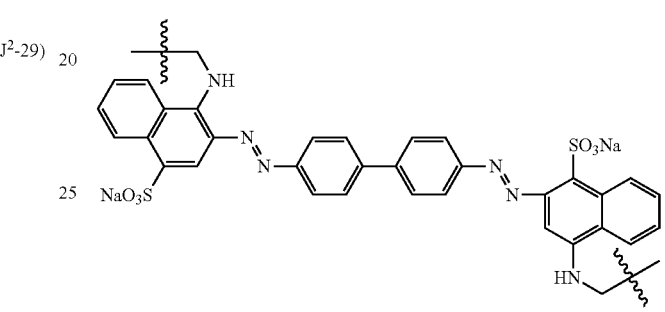
(J²-34)
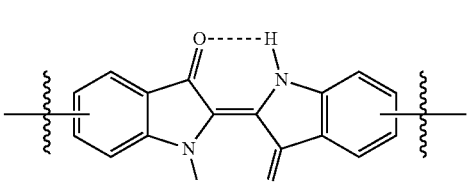
(J²-35)
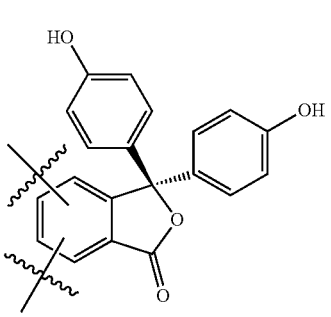
(J²-36)
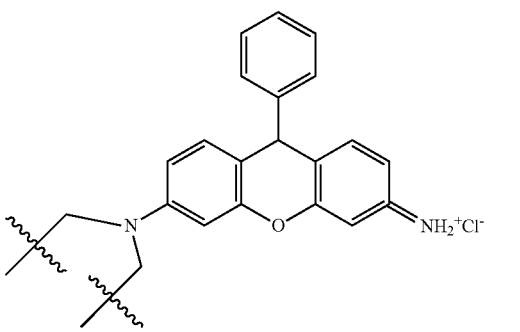

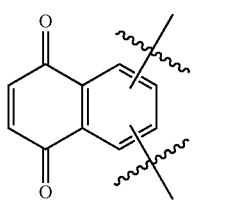 (J²-37)
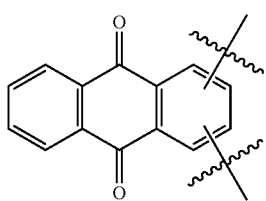 (J²-38)
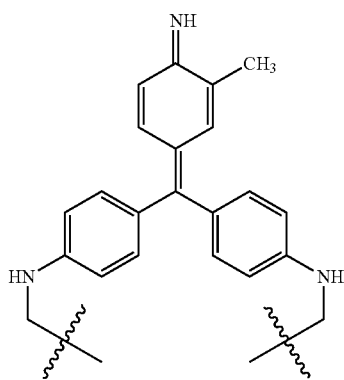 (J²-39)
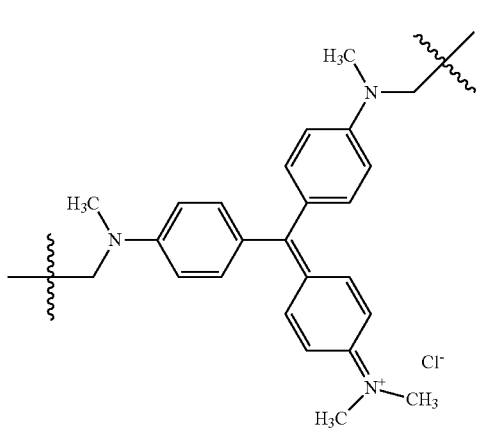 (J²-40)
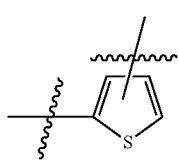 (J²-41)
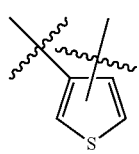 (J²-42)
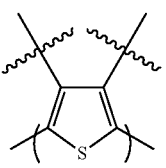 (J²-43)
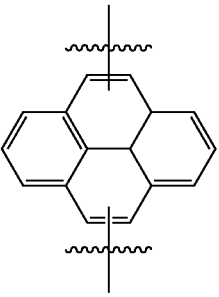 (J²-44)
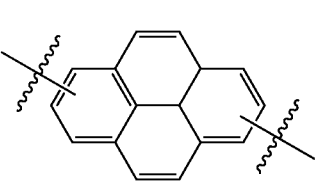 (J²-45)
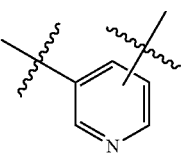 (J²-46)
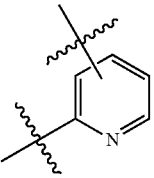 (J²-47)
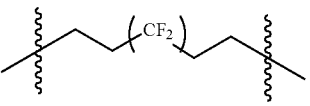 (J²-48)
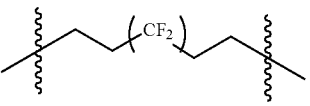 (J²-49)
Advantageously, for the groups of formulae (J²-3), (J²-5), (J²-8), (J²-9), (J²-10), (J²-18), (J²-19), (J²-20), (J²-21), (J²-22) and (J²-27), the binding with the triazole groups is accomplished with an alkylene chain comprising from 0 to 15, preferably from 0 to 12 units —(CH$_2$)—.
Advantageously, for the group of formula (J²-43), the number of units

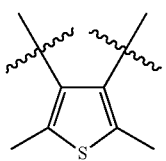

ranges from 1 to 20.

Advantageously, for the group of formula (J²-48), the number of units —CF₂— ranges from 4 to 18.

According to the invention, J³ may represent a mono- or poly-functional group comprising at least one functional group selected from:

- a decontaminating complexing group selected from a triarylphosphine and derivatives thereof,
- a group allowing molecular recognition selected from a melamine and derivatives thereof,
- a structuring group such as a phenylene.

Advantageously, J³ represents a group of formulae (J³-1) to (J³-3)

(J³-1)

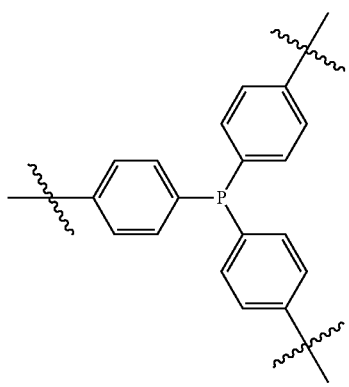

(J³-2)

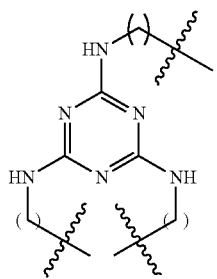

(J³-3)

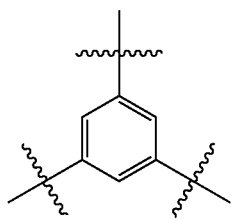

Advantageously, for the group of formula (J³-2), the binding with the triazole groups is accomplished with an alkylene chain comprising from 0 to 15, preferably from 0 to 12 units —(CH₂)—.

According to the invention, J⁴ may represent a mono- or poly-functional group comprising at least one functional group selected from:

- a colouring group selected from a porphyrin, a phthalocyanin, an azinic, an azoic, an indigoid, a triphenylmethane, a polyaromatic and derivatives thereof;
- a decontaminating complexing group selected from a malonamide and derivatives thereof;
- a catalyst group selected from trans-1,2-diaminocyclohexane, 1,2-diphenylenediamine and derivatives thereof;
- a redox group selected from 1,4-(4-aminophenyl)-butadiene and derivatives thereof;
- a structuring group such as a phenylene.

Advantageously, J⁴ represents a group of formulae (J⁴-1) to (J⁴-15)

(J⁴-1)

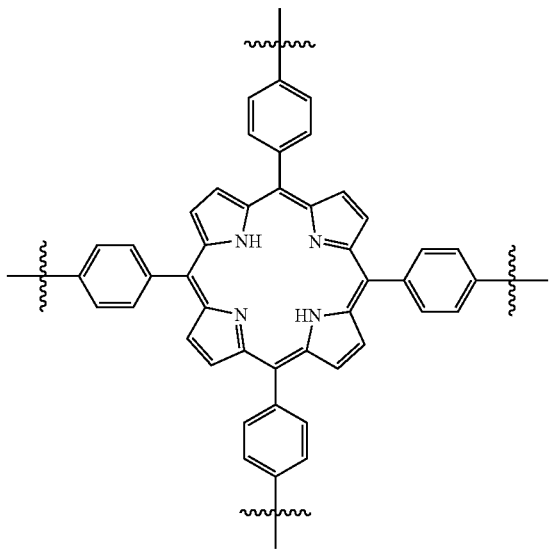

(J⁴-2)

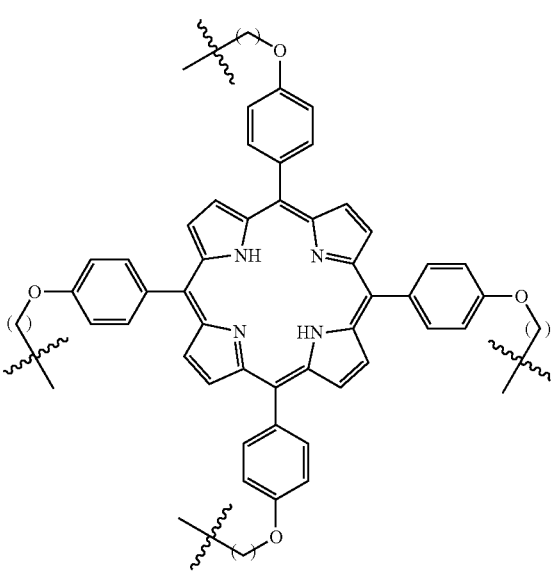

(J⁴-3)
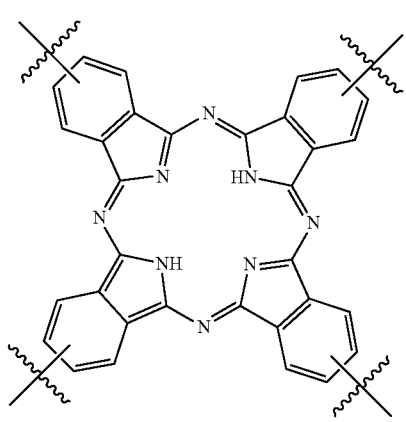
(J⁴-4)
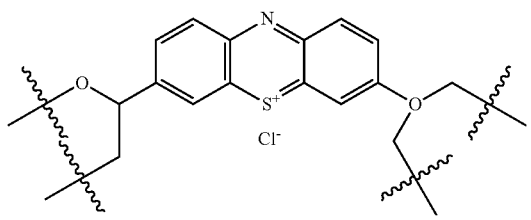
(J⁴-5)
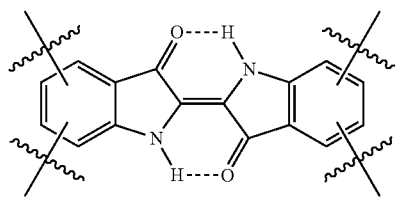
(J⁴-6)
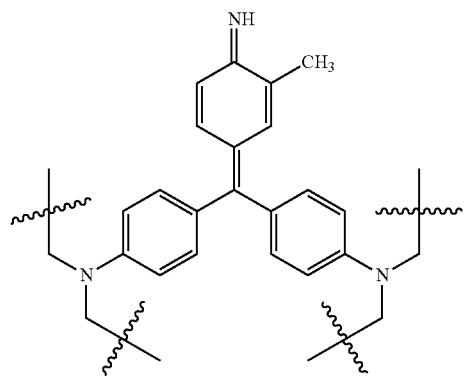
(J⁴-7)
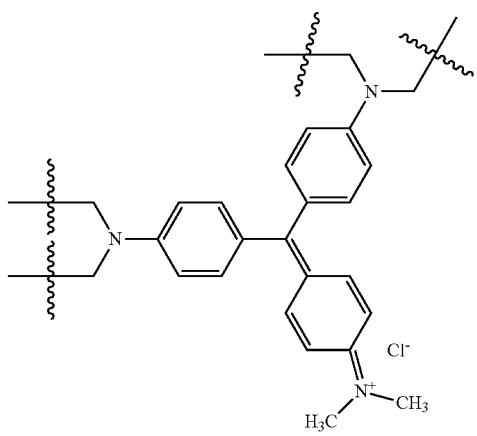
(J⁴-8)
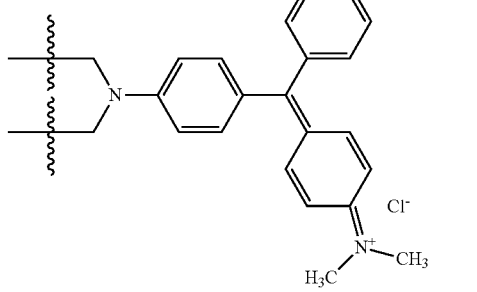
(J⁴-9)
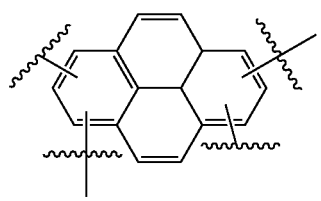
(J⁴-10)
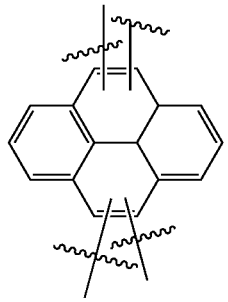
(J⁴-11)
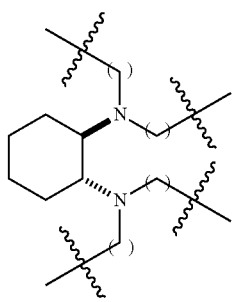

-continued (J⁴-12)

(J⁴-13)

(J⁴-14)

(J⁴-15)

Advantageously, for the groups of formulae (J⁴-2), (J²-10), (J⁴-11) and (J⁴-12), the binding with the triazole groups is accomplished with an alkylene chain comprising from 0 to 15, preferably from 0 to 12 units —(CH$_2$)—.

Another object of the present invention relates to a method for preparing a compound of formula (II)

$$R^1[(E^1)_jO]_d \quad R^2[(E^2)_kO]_e—Si\{A\}_a U\{\{\}_q V\}_c B\}_b Si—[O(E^5)_n]_hR^5 \quad R^3[(E^3)_lO]_f \quad [O(E^6)_o]_iR^6 \quad [O(E^4)_m]_gR^4$$ (II)

wherein:
U represents a group U², U⁴, U⁶ or U⁸;
V represents a group V², V⁴, V⁶ or V⁸;
the whole of the different characteristics or preferences for R¹, R², R³, R⁴, R⁵, R⁶, E¹, E², E³, E⁴, E⁵, E⁶, A, B, Q, U², U⁴, U⁶, U⁸, V², V⁴, V⁶, V⁸, a, b, d, e, f, g, h, i, j, k, l, m, n, o and q apply to the compound of formula (II) obtained by the method according to the invention;
by the reaction between a compound of formula (XV)

$$R^1[(E^1)_jO]_d \quad R^2[(E^2)_kO]_e—Si\{A\}_a (U^4)\{\}_q (V^4)\}_c B\}_b Si—[O(E^5)_n]_hR^5 \quad R^3[(E^3)_lO]_f \quad [O(E^6)_o]_iR^6 \quad [O(E^4)_m]_gR^4$$ (XV)

wherein:
the whole of the different characteristics or preferences for R¹, R², R³, R⁴, R⁵, R⁶, E¹, E², E³, E⁴, E⁵, E⁶, A, B, Q, a, b, c, d, e, f, g, h, i, j, k, l, m, n, o and q apply to the compound of formula (XV),
U$^A$ represents a group selected from the groups of formula:

N—(E⁷)$_p$—≡≡≡ (U$^{A1}$)

S⁺—(E⁷)$_p$—≡≡≡CH, Z⁻ (U$^{A2}$)

N⁺—[(E⁷)$_p$—≡≡≡CH,]$_2$ Z⁻ (U$^{A3}$)

N⁺(T¹)—(E⁷)$_p$—≡≡≡, Z⁻ (U$^{A4}$)

wherein the whole of the characteristics for E⁷, T¹, Z⁻ and p apply to the groups (U$^{A1}$), (U$^{A2}$), (U$^{A3}$) and (U$^{A4}$);
V$^A$ represents a group selected from the groups of formula.

N—(E¹²)$_w$—≡≡≡ (V$^{A1}$)

S⁺—(E¹²)$_w$—≡≡≡, Z⁻ (V$^{A2}$)

N⁺—[(E¹²)$_w$—≡≡≡CH]$_2$, Z⁻ (V$^{A3}$)

N⁺(T²)—(E¹²)$_w$—≡≡≡, Z⁻ (V$^{A4}$)

wherein the whole of the characteristics for E¹², T², Z⁻ and w apply to the groups (V$^A$), (V$^{A2}$), (V$^{A3}$) and (V$^{A4}$);
and a compound of formula (XVI)

J-N₃ (XVI)

wherein the whole of the characteristics for J apply to the compound of formula (XVI); in the presence of a catalyst based on copper.
According to the invention, the catalyst based on copper may be selected from a halogenated derivative or a carbonaceous derivative of copper.

As examples of halogenated copper derivatives, mention may be made of copper iodide CuI or copper iodide complexed with tris(1,2,3-triazolyl)methyl amine, tris(1-benzyl-1H-1,2,3-triazol-4-yl)methyl amine (TBTA), tris(1-tert-butyl-1H-1,2,3-triazol-4-yl)methyl amine (TTTA) or tris (benzimidazole)methyl amine (TBIA) (cf. Hein et al, Chem. Soc. Rev., 2010, 39, 1302-1315).

As examples of carbonaceous derivatives of copper, mention may be made of the complex of formula Cu(NHC)X wherein NHC is a N-heterocyclic carbene and X represents a halogen.

Advantageously, the catalyst based on copper is bromo tris(triphenylphosphine) copper (I) of formula [CuBr(PPh$_3$)$_3$]

According to the invention, the compound (II) may be obtained from the reaction between an equivalent of a compound of formula (XV) and (c+1) equivalents of compound of formula (XVI) in solution.

According to the invention, the definition of c is identical with the definition of c defined for the compound of formula (XV) and may thus represent 0, 1, 2 or 3.

According to the invention, the solution comprises a mixture of solvents. Advantageously, the solution comprises a 1:1 mixture of dry tetrahydrofurane and triethylamine.

According to the invention, the molar concentration of a compound of formula (XV) in the solution may range from 0.01 to 5 mol/L, preferably from 0.5 to 2 mol/L.

According to the invention, the molar concentration of the compound of formula (XVI) in the solution may range from 0.01 to 5 mol/L, preferably from 0.5 to 2 mol/L.

According to the invention, the molar content of a catalyst based on copper in the solution may range from 0.5 to 5% relatively to the compound of formula (XV).

According to the invention, the reaction occurs at 100° C. under microwave irradiation (maximum power 200 W) for 1 to 20 minutes or else between 15 and 25° C. for 24 h.

Another object of the present invention relates to a method for preparing a compound of formula (II)

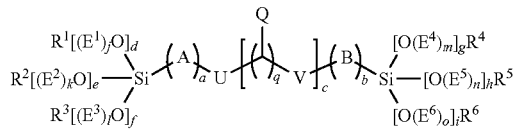
(II)

wherein:
U represents a group $U^1$, $U^3$, $U^5$ or $U^7$;
V represents a group $V^1$, $V^3$, $V^5$ or $V^7$;
the whole of the characteristics or preferences for $R^1$, $R^2$, $R^3$, $R^4$, $R^5$, $R^6$, $E^1$, $E^2$, $E^3$, $E^4$, $E^5$, $E^6$, A, B, Q, $U^1$, $U^3$, $U^5$, $U^7$, $V^1$, $V^3$, $V^5$, $V^7$, a, b, d, e, f, g, h, i, j, k, l, m, n, o and q apply to the compound of formula (II);
by the reaction between a compound of formula (XVII)

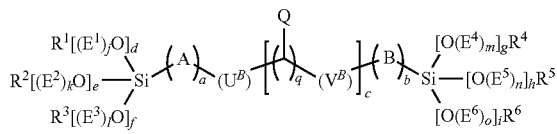
(XVII)

wherein:
the whole of the characteristics or preferences for $R^1$, $R^2$, $R^3$, $R^4$, $R^5$, $R^6$, $E^1$, $E^2$, $E^3$, $E^4$, $E^5$, $E^6$, A, B, Q, a, b, c, d, e, f, g, h, i, j, k, l, m, n, o and q apply to the compound of formula (XVII);
$U^B$ represents a group selected from the groups of formula:

 (U$^{B1}$)

 (U$^{B2}$)

 (U$^{B3}$)

 (U$^{B4}$)

wherein the whole of the characteristics for $E^7$, $Z^-$ and p apply to the groups ($U^{B1}$), ($U^{B2}$), ($U^{B3}$) and ($U^{B4}$)
$V^B$ represents a group selected from the groups of formula:

 (V$^{B1}$)

 (V$^{B2}$)

 (V$_{B3}$)

 (V$^{B4}$)

wherein the whole of the characteristics for $E^{12}$, $Z^-$ and w apply to the groups ($V^{B1}$), ($V^{B2}$), ($V^{B3}$) and ($V^{B4}$);
and a compound of formula (XVIII)

 (XVIII)

wherein the whole of the characteristics shown for J apply to the compound of formula (XVIII);
in the presence of a catalyst based on copper.

According to the invention, the catalyst based on copper may be selected from a halogenated derivative or a carbonaceous derivative of copper.

As examples of halogenated derivatives of copper, mention may be made of copper iodide CuI or copper iodide complexed with tris(1,2,3-triazolyl)methyl amine, tris(1-benzyl-1H-1,2,3-triazol-4-yl)methyl amine (TBTA), tris(1-tert-butyl-1H-1,2,3-triazol-4-yl)methyl amine (TTTA) or tris(benzimidazole)methyl amine (TBIA) (C F Hein et al, Chem. Soc. Rev., 2010, 39, 1302-1315).

As examples of carbonaceous derivatives of copper, mention may be made of the complex of formula Cu(NHC)X wherein NHC is an N-heterocyclic carbene and X represents a halogen Advantageously, the copper catalyst is bromo-tris(triphenylphosphine) copper (I) of formula [CuBr(PPh$_3$)$_3$]

According to the invention, the compound of formula (II) may be obtained from the reaction between an equivalent of a compound of formula (XVII) and c+1 equivalents of a compound of formula (XVIII) in a solution.

According to the invention, the definition of c is identical with the definition of c for the compound of formula (XVII) and may thus represent 0, 1, 2 or 3.

According to the invention, the solution comprises a mixture of solvents. Advantageously, the solution comprises a 1:1 mixture of dry tetrahydrofurane and triethylamine.

According to the invention, the molar concentration of a compound of formula (XVII) in the solution may range from 0.01 to 5 mol/L, preferably from 0.5 to 2 mol/L.

According to the invention, the molar concentration of a compound of formula (XVIII) in the solution may range from 0.01 to 5 mol/L, preferably from 0.5 to 2 mol/L.

According to the invention, the molar content of a catalyst based on copper in the solution ranges from 0.5 to 5% relatively to the compound (XVII).

According to the invention, the reaction occurs at 100° C. under microwave irradiation (maximum power 200 W) for 1 to 20 minutes or else between 15 and 25° C. for 24 h.

Another object of the present invention relates to a method for preparing a compound of formula (XII) comprising the hydrolysis of a compound of formula (XIX)

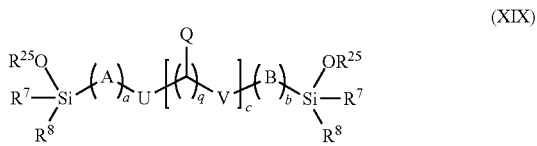

(XIX)

wherein the whole of the characteristics or preferences for $R^7$, $R^8$, A, U, Q, V, B, a, b, c and q apply to the compound of formula (XIX).

According to the invention, $R^{25}$ may represent a hydrogen atom, a $C_1$-$C_6$-alkyl group, an aryl group, a $C_1$-$C_6$-alkoxy group, a $C_3$-$C_8$-alkylene-alkenyl group.

According to the invention, the compound of formula (XII) may be obtained according to a method (P1).

According to the invention, the method (P1) comprises the putting into a solution of the compound of formula (XIX) in the presence of water, a catalyst and optionally in the presence of a surfactant.

According to the invention, the catalyst may be selected from an acid catalyst, a basic catalyst or a nucleophilic catalyst.

According to the invention, the surfactant may be selected from ammonium and phosphonium salts including at least one long alkyl chain, preferably the surfactant is sodium hexadecyl sulfate (SHS) containing 40% by weight of sodium stearyl sulfate based on the total weight of the surfactant.

According to the invention, the reaction may occur with or without any organic solvent.

According to the invention, the solvent may be selected from water, alcohols comprising from 1 to 8 carbon atoms, ethyl ether, THF, DMF or DMSO.

According to the invention, the alcohols comprising 1 to 8 carbon atoms are selected from methanol, ethanol or propan-1-ol.

According to the invention, the reaction occurs at a temperature ranging from 20 to 100° C.

According to the invention, the reaction is conducted until a gel or a precipitate is obtained and then the final material is left to age for 2 to 7 days.

According to the invention, the compound of formula (XII) may also be obtained by a method (P2).

According to the invention, the method (P2) comprises the co-hydrolysis of the compound of formula (XIX) with a silica source such as tetramethylorthosilicate (TMOS) or tetraethylorthosilicate (TEOS) or with another polysilylated organosilane, such as 1,4-bistrialkoxysilylethane (BTSE; alkoxy=methoxy or ethoxy) or 1,4-bistrialkoxysilylbenzene (BTSB; alkoxy=methoxy or ethoxy).

The characteristics of the solvent, of the catalyst and of the temperature shown for the method (P1) apply to the method (P2).

According to the invention, the method (P2) may give the possibility of ending up with a siloxane-silica composite material of the (IX); $xSiO_2$, type and siloxane-silsesquioxane (SQ) such as a composite (IX); BTSE-SQ or a composite (IX); BTSB-SQ.

According to the invention, a composite (XII)-BTSE-SQ may be defined by the following formula:

$$O_{1,5}Si—(CH_2)_2—SiO_{1,5} \qquad \text{XII;}$$

wherein the oxygen atom of the terminal group $SiO_{1/2}$ of the compound of formula (XII) is bound to an oxygen atom of the terminal group $SiO_{1,5}$ of BTSE.

According to the invention, a composite (XII)-BTSB-SQ may be defined by the following formula:

$$O_{1,5}Si\text{-Ph-}SiO_{1,5} \qquad \text{XII;}$$

wherein the oxygen atom of the terminal group $SiO_{1/2}$ of the compound of formula (XII) is bound to an oxygen atom of the terminal group $SiO_{1,5}$ of BTSB.

According to the invention, the compound of formula (XII) may be obtained by a method (P3).

According to the invention, the method (P3) comprises the co-hydrolysis of the compound of formula (XIX) with a silicone source such as diethoxydimethylsilane.

The characteristics of the solvent, of the catalyst and of the temperature for the method (P1) apply to the method (P3).

According to the invention, the method (P3) may give the possibility of ending up with a siloxane-silicone composite polymer of the type (XII); $xMe_2SiO$.

Another object of the present invention relates to a method for preparing a compound of formula (XIII) comprising the hydrolysis of a compound of formula (XX)

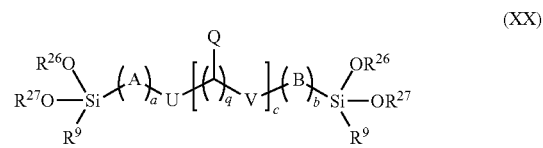

(XX)

wherein the whole of the characteristics or preferences for $R^9$, A, U, Q, V, B, a, b, c and q apply to the compound of formula (XX).

According to the invention, $R^{26}$ and $R^{27}$, either identical or different, may represent a hydrogen atom, a $C_1$-$C_6$-alkyl group, an aryl group, a $C_1$-$C_6$-alkoxy group, a $C_3$-$C_8$-alkylene-alkenyl group.

According to the invention, the compound of formula (XIII) may be obtained by the method (P1) or (P2) applied to the compound of formula (XX).

According to the invention, the method (P2) gives the possibility of ending up with a siloxane-silica composite material of the type (XIII); $xSiO_2$, and silicone-silsesquioxane (SQ) composite material such as a composite (XIII); BTSE-SQ or a composite (XIII); BTSB-SQ.

Another object of the present invention relates to a method for preparing a compound of formula (XIV) comprising the hydrolysis of a compound of formula (XXI)

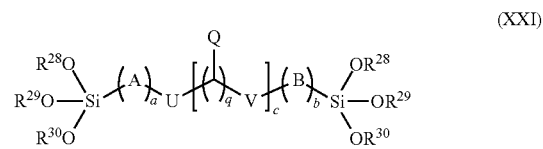

(XXI)

wherein the whole of the characteristics or preferences for A, U, Q, V, B, a, b, c and q apply to the compound of formula (XXI).

According to the invention, $R^{28}$, $R^{29}$ and $R^{30}$, either identical or different, may represent a hydrogen atom, a $C_1$-$C_6$-alkyl group, an aryl group, a $C_1$-$C_6$-alkoxy group, a $C_3$-$C_8$-alkylene-alkenyl group.

According to the invention, the compound of formula (XIV) may be obtained by the method (P1) or (P2) applied to the compound of formula (XXI).

According to the invention, the method (P2) may give the possibility of ending up with a siloxane-silica composite material of the type (XIV); $xSiO_2$, and a siloxane-silsesquioxane (SQ) composite material such as a composite (XIV); BTSE-SQ or a composite (XIV); BTSB-SQ.

The different objects of the invention and their embodiments will be better understood upon reading the examples which follow. These examples are given as an indication, without any limitation.

All the experiments are carried out by using standard Schlenk techniques under an inert atmosphere.

The NMR spectra were obtained in solution on Bruker apparatuses operating at 400 or 250 MHz, in dry $CDCl_3$ at 298 K.

The NMRs in the solid state were measured on a Varian ASX400 apparatus.

The chemical shifts in $^1H$, $^{29}Si$ and $^{13}C$ are reported in ppm relatively to $Me_4Si$.

The high resolution mass spectra were obtained by electrospray ionization.

The infrared spectra were obtained by ATR on a Perkin 100 spectrometer.

EXAMPLE 1: PREPARATION OF POLYSILYLATED ORGANOSILANE COMPOUNDS ACCORDING TO THE INVENTION

All the exemplified polysilylated organosilane compounds were obtained by the reaction between:
a compound 1 of formula

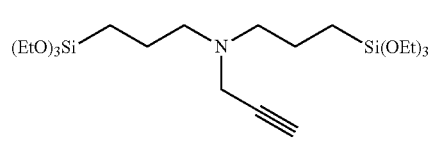

1 and an organic nitride.

In a micro-wave reactor, were introduced the compound 1 (2.0 mmol), the organic nitride (2.0 mmol of nitride function), the catalyst $[CuBr(PPh_3)_3]$, in a 1:1 mixture $THF/Et_3N$ (1 ml).

The mixture was irradiated at 100° C. for the indicated time, and then the volatile compounds were evaporated. After extraction with pentane (3×2 ml) and then concentration, the compounds 2 to 11 were obtained.

Table I shows the structures of the organic nitrides used and the structures of the corresponding polysilylated organosilane compounds 2 to 11.

TABLE I

| Organic nitrides | Polysilylated organosilane compounds |
|---|---|

TABLE I-continued
| Organic nitrides | Polysilylated organosilane compounds |
|---|---|
| 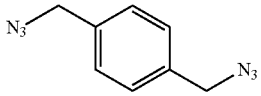 [SMILES: [N-]=[N+]=NCc1ccc(CN=[N+]=[N-])cc1] | 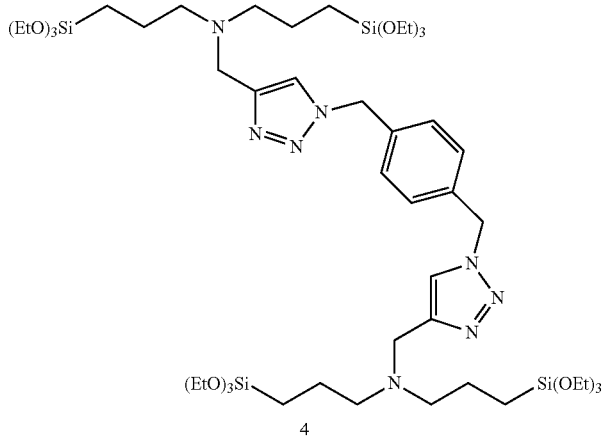<br>4 |
| 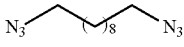 | 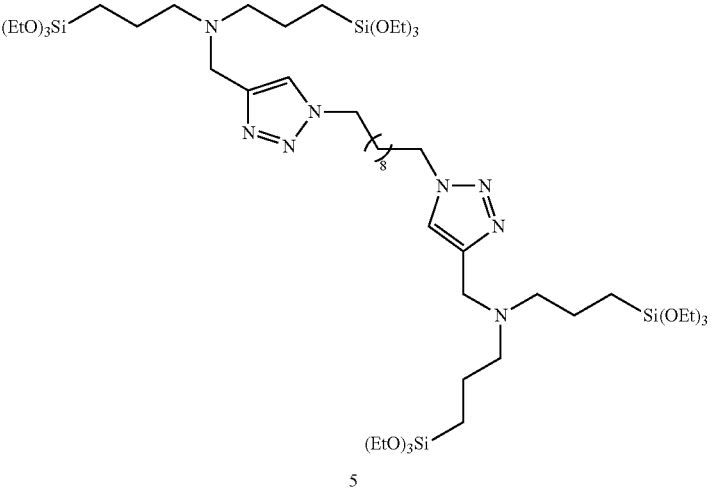<br>5 |
| 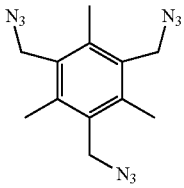 [SMILES: Cc1c(CN=[N+]=[N-])c(C)c(CN=[N+]=[N-])c(C)c1CN=[N+]=[N-]] | 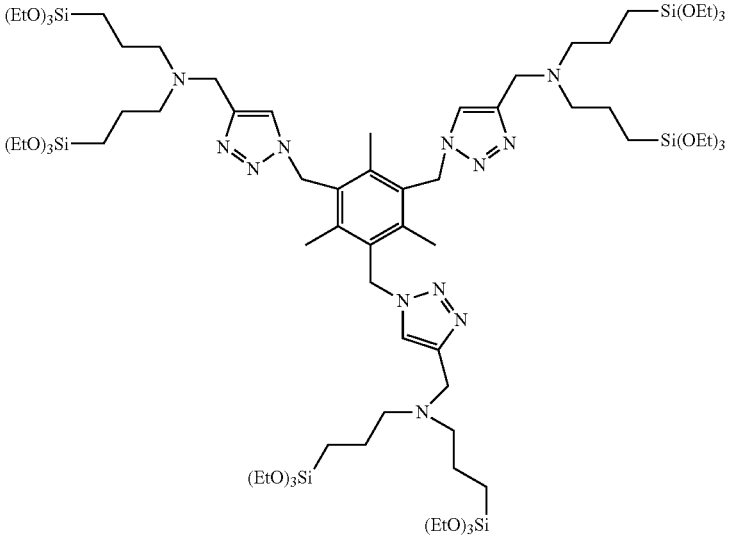<br>6 |

TABLE I-continued

| Organic nitrides | Polysilylated organosilane compounds |
|---|---|

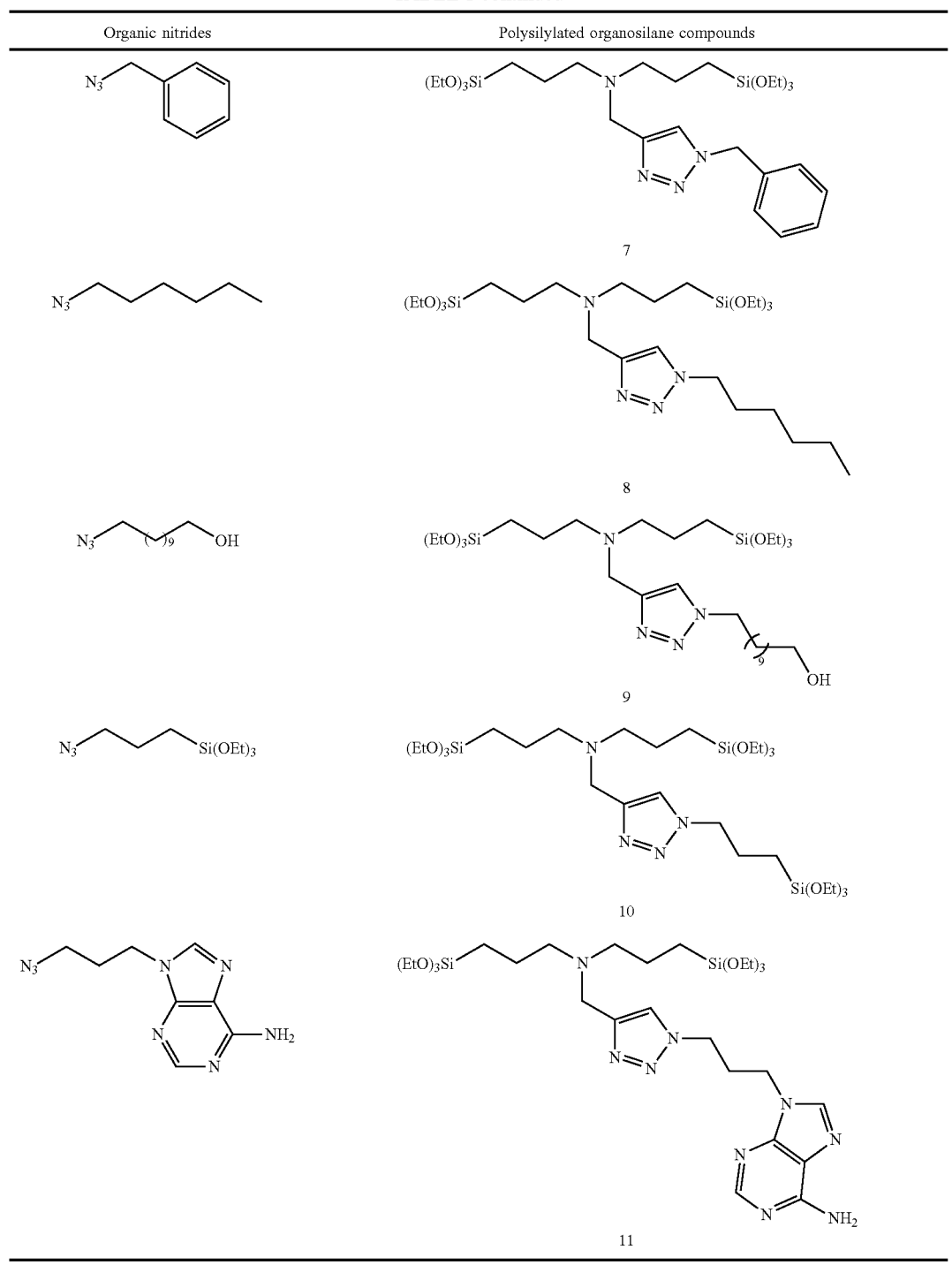

The characteristics of each reaction ending up with the compounds 2 to 11, as well as the NMR characterisation of each obtained product are described.

Compound 2

Cat 0.5%; time: 10 min; yield: 97%.

$^1$H NMR (400 MHz, CDCl$_3$) δ=7.41 (s, 1H), 4.59-4.40 (m, 2H), 4.10-3.90 (m, 4H), 3.71 (t, J=7.0 Hz, 12H), 3.67 (s, 2H), 2.44-2.9 (m, 6H), 1.49 (m, 4H), 1.24 (t, J=7.1 Hz, 6H), 1.12 (t, J=7.0 Hz, 18H), 0.57-0.34 (m, 4H). $^{13}$C NMR (101 MHz, CDCl$_3$) δ=145.9, 122.4, 62.0, 58.2, 56.6, 48.8, 44.3, 27.9, 26.5, 20.4, 18.2, 16.3, 7.8.

HRMS (ESI$^+$):

m/z calculated for C$_{27}$H$_{60}$N$_4$O$_9$Si$_2$P, 671.3637 m/z determined: 671.3635.

Compound 3

Cat: 0.5%; time: 5 min; yield: 96%.

$^1$H NMR (400 MHz, CDCl$_3$) δ=8.19-7.94 (m, 8H), 7.83 (d, J=7.8 Hz, 1H), 7.19 (s, 1H), 6.14 (s, 2H), 3.71 (q, J=7.0 Hz, 12H), 3.66 (s, 2H), 2.42-2.21 (m, 4H), 1.56-1.39 (m, 4H), 1.13 (t, J=7.0 Hz, 18H), 0.55-0.37 (m, 4H). $^{13}$C NMR (101 MHz, CDCl$_3$) δ=146.1, 132.0, 131.1, 130.5, 129.2, 128, 128.2, 127.4, 127.2, 127.1, 126.3, 125.8, 125.7, 125.0, 124.9, 124.4, 122.2, 121.9, 58.2, 56.6, 52.3, 48.8, 20.3, 18.2, 7.8.

HRMS (ESI$^+$):
m/z calculated for $C_{38}H_{57}N_4O_6Si$: 721.3817;
m/z determined: 721.3830.

Compound 4
Cat: 0.5%; time: 10 min; yield: 91%.
$^1$H NMR (250 MHz, CDCl$_3$) δ=7.37 (bs, 2H), 7.23 (s, 4H), 5.49 (s, 4H), 3.81 (q, J=7.0 Hz, 24H), 3.77 (s, 4H), 2.47-2.32 (m, 8H), 1.69-1.40 (m, 8H), 1.19 (t, J=7.0 Hz, 36H), 0.61-0.44 (m, 8H). $^{13}$C NMR (101 MHz, CDCl$_3$) δ=146.2, 135.4, 128.5, 122.2, 58.2, 56.6, 53.3, 48.8, 20.3, 18.2, 7.8.

HRMS (ESI$^+$)
m/z calculated for $C_{50}H_{99}N_8O_{12}Si_4$: 1115.6460;
m/z determined: 1115.6447.

Compound 5
Cat: 0.5%; time: 5 min; yield: 87%.
$^1$H NMR (250 MHz, CDCl$_3$) δ=7.38 (s, 2H), 4.26 (t, J=7.3 Hz, 4H), 3.75 (q, J=7.0 Hz, 24H), 3.71 (s, 4H), 2.45-2.30 (m, 8H), 1.92-1.75 (m, 4H), 1.63-1.43 (m, 8H), 1.30-1.20 (bs, 12H), 1.36 (t, J=7.0 Hz, 36H), 0.58-0.45 (m, 8H). $^{13}$C NMR (101 MHz, CDCl$_3$) δ=145.8, 122.0, 58.3, 56.7, 50.1, 48.9, 30.3, 29.2, 28.9, 26.4, 20.4, 18.3, 7.9.

HRMS (ESI$^+$):
m/z calculated for $C_{52}H_{111}N_8O_{12}Si_4$: 1151.7399;
m/z determined: 1151.7421.

Compound 6
Cat: 1%; time: 15 min; yield: 90%.
$^1$H NMR (400 MHz, CDCl$_3$) δ=7.17 (s, 3H), 5.67 (s, 2H), 5.64 (s, 4H), 3.82 (q, J=7.0 Hz, 36H), 3.74 (s, 6H), 2.61-2.31 (m, 21H), 1.67-1.46 (m, 12H), 1.23 (t, J=7.0 Hz, 54H), 0.66-0.41 (m, 12H). $^{13}$C NMR (101 MHz, CDCl$_3$) δ=146.0, 139.6, 130.7, 121.7, 58.2, 56.6, 48.9, 20.2, 18.2, 16.5, 7.9, 0.9.

Compound 7
Cat: 0.5%; time: 5 min; yield: 95%.
$^1$H NMR (400 MHz, CDCl$_3$) δ=7.38-7.31 (m, 5H), 7.25-7.20 (m, 1H), 5.50 (s, 2H), 3.78 (q, J=7.0 Hz, 12H), 3.74 (s, 2H), 2.44-2.34 (m, 4H), 1.62-1.46 (m, 4H), 1.19 (t, J=7.0 Hz, 18H), 0.59-0.48 (m, 4H). $^{13}$C NMR (101 MHz, CDCl$_3$) δ=146.5, 135.0, 129.1, 128.7, 128.0, 122.3, 58.3, 56.8, 54.1, 49.0, 20.5, 18.4, 8.0.

HRMS (ESI$^+$):
m/z calculated for $C_{28}H_{53}N_4O_6Si_2$: 597.3504;
m/z determined: 597.3514.

Compound 8
Cat: 0.5%; time: 24 h at room temperature; yield: 94%.
$^1$H NMR (400 MHz, CDCl$_3$) δ=7.37 (s, 1H), 4.27 (t, J=7.3 Hz, 2H), 3.76 (q, J=7.0 Hz, 12H), 3.72 (s, 2H), 2.42-2.34 (m, 4H), 1.88-1.77 (m, 3H), 1.58-1.48 (m, 4H), 1.26 (bs, 8H), 1.17 (t, J=7.0 Hz, 18H), 0.57-0.49 (m, 4H). $^{13}$C NMR (101 MHz, CDCl$_3$) δ=145.9, 122.0, 58.3, 56.8, 50.2, 49.0, 31.2, 30.3, 26.2, 22.4, 20.5, 18.3, 13.9, 8.0.

HRMS (ESI$^+$):
m/z calculated for $C_{27}H_{59}N_4O_6Si_2$: 591.3973;
m/z determined: 591.3969.

Compound 9
Cat: 1%; time: 15 min; yield: 95%.
$^1$H NMR (400 MHz, CDCl$_3$) δ=7.41 (s, 1H), 4.30 (t, J=7.3 Hz, 2H), 3.80 (q, J=7.0 Hz, 12H), 3.76 (s, 2H), 3.62 (t, J=6.6 Hz, 2H), 2.63-2.55 (m, 1H), 2.42 (t, J=8.0 Hz, 4H), 1.92-1.82 (m, 2H), 1.65-1.49 (m, 4H), 1.37-1.23 (b, 14H), 1.21 (t, J=7.0 Hz, 18H), 1.07 (t, J=7.2 Hz, 2H), 0.61-0.53 (m, 4H).

$^{13}$C NMR (101 MHz, CDCl$_3$) δ=145.9, 122.1, 63.0, 58.4, 56.8, 50.3, 49.1, 32.9, 30.4, 29.5, 29.4 (3C), 29.0, 26.5, 25.8, 20.5, 18.4, 8.0.

HRMS (ESI$^+$):
m/z calculated for $C_{32}H_{69}N_4O_7Si_2$: 677.4705;
m/z determined: 677.4698.

Compound 10
Cat: 1%; time: 20 min; yield: 94%.
$^1$H NMR (400 MHz, CDCl$_3$) δ=7.41 (s, 1H), 4.30 (t, J=7.2 Hz, 2H), 3.78 (t, J=7.0 Hz, 12H), 3.77 (t, J=7.0 Hz, 6H), 3.75 (s, 2H), 2.41 (t, J=780 Hz, 4H), 2.03-1.94 (m, 2H), 1.63-1.48 (m, 4H), 1.19 (t, J=7.0 Hz, 9H), 1.18 (t, J=7.0 Hz, 18H), 0.62-0.51 (m, 6H). $^{13}$C NMR (101 MHz, CDCl$_3$) δ=145.6, 122.3, 58.6, 58.4, 56.8, 52.5, 49.0, 24.4, 20.5, 18.4 (2C), 8.0, 7.6.

HRMS (ESI$^+$):
m/z calculated for $C_{30}H_{67}N_4O_9Si_3$: 711.4216;
m/z determined: 711.4212.

Compound 11
Cat: 1%; time: 10 min; yield: 91%.
$^1$H NMR (400 MHz, CDCl$_3$) δ=8.33 (s, 1H), 7.91 (s, 1H), 7.52 (s, 1H), 6.14 (s, 2H). 4.32 (t, J=6.4 Hz, 2H), 4.23 (t, J=6.5 Hz, 2H), 3.77 (q, J=7.0 Hz, 12H), 3.73 (s, 2H), 2.52-2.46 (m, 2H), 2.44-2.36 (m, 4H), 1.60-1.49 (m, 4H), 1.17 (t, J=7.0 Hz, 18H), 0.58-0.50 (m, 4H), $^{13}$C NMR (101 MHz, CDCl$_3$) δ=155.8, 153.1, 146.4, 132.2, 132.1, 128.6, 122.7, 58.3, 56.9, 49.0, 46.8, 40.9, 30.5, 20.6, 18.4, 8.0.

HRMS (ESI$^+$):
m/z calculated for $C_{29}H_{56}N_9O_6Si_2$: 682.3892;
m/z determined: 682.3894.

EXAMPLE 2: PREPARATION OF POLYSILYLATED ORGANOSILANE COMPOUNDS ACCORDING TO THE INVENTION

All the exemplified polysilylated organosilane compounds were obtained by the reaction between:
a compound of formula 12

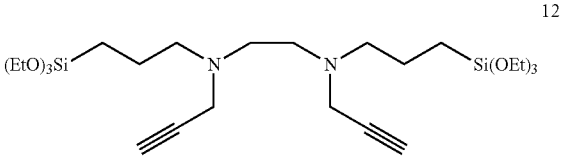

and an organic nitride.

In a microwave reactor were introduced the compound 12 (2.0 mmol), the organic nitride (4.0 mmol of nitride function), the catalyst [CuBr(PPh$_3$)$_3$], in a 1:1 mixture THF/Et$_3$N (1 ml).

The mixture was irradiated at 100° C. for the indicated time, and then the volatile compounds were evaporated. After extraction with pentane (3×2 ml) and then concentration, the products 13 and 14 were obtained.

Table II shows the structures of the organic nitrides used and the structures of the corresponding polysilylated organosilane compounds 13 and 14.

TABLE II

| Organic nitrides | Polysilylated organosilane compounds |
|---|---|
| $N_3$–CH$_2$–Ph | Compound 13: (EtO)$_3$Si–(CH$_2$)$_3$–N(CH$_2$-triazole-CH$_2$-Ph)–CH$_2$CH$_2$–N(CH$_2$-triazole-CH$_2$-Ph)–(CH$_2$)$_3$–Si(OEt)$_3$ |
| Pyrene-CH$_2$–N$_3$ | Compound 14: analogous bis-triazole with pyrenylmethyl groups |
| $N_3$–CH$_2$–C(O)–O–Et | Compound 22: analogous bis-triazole with –CH$_2$–C(O)OEt groups |

The characteristics of each reaction ending up with the compound 13, 14 and 22 as well as the NMR characterisation of each obtained product, are described.

Compound 13

Cat: 0.5%; time: 10 min; yield: 90%.

$^1$H NMR (400 MHz, CDCl$_3$) δ=7.44-7.28 (m, 8H), 7.26-7.21 (m, 4H), 5.49 (s, 4H), 3.77 (q, J=7.0 Hz, 12H), 3.70 (s, 4H), 2.52 (s, 4H), 2.41-2.35 (m, 4H), 1.59-1.47 (m, 4H), 1.19 (t, J=7.0 Hz, 18H), 0.55-0.48 (m, 4H). $^{13}$C NMR (63 MHz, CDCl$_3$) δ=145.8, 134.9, 129.0, 128.5, 127.9, 122.5, 58.2, 57.4, 53.9, 51.7, 49.0, 20.4, 18.3, 7.8.

HRMS (ESI$^+$):

m/z calculated for $C_{40}H_{67}N_8O_6Si_2$: 811.4722;

m/z determined: 811.4726

Compound 14

Cat 0.5%, time: 20 min, yield: 94%.

$^1$H NMR (400 MHz, CDCl$_3$) δ=8.18-7.80 (m, 18H), 7.89 (s, 2H), 6.10 (s, 4H), 3.69 (q, J=7.0 Hz, 12H), 3.49 (s, 4H), 2.36 (s, 4H), 2.22 (t, J=4 Hz, 4H), 1.45-1.42 (m, 4H), 1.12 (t, J=7.0 Hz, 18H), 0.42-0.34 (m, 4H). $^{13}$C NMR (101 MHz, CDCl$_3$) δ=145.8, 131.9, 131.1, 130.5, 129.1, 128.8, 128.1, 127.4, 127.3, 127.2, 126.3, 125.8, 125.7, 124.9 (2C), 124.4, 122.6, 122.0, 58.3, 57.4, 53.1, 52.2, 48.9, 20.2, 18.3, 7.8.

HRMS (ESI$^+$):

m/z calculated for $C_{60}H_{75}N_8O_6Si_2$: 1059.5348;

m/z determined: 1059.5354.

Compound 22

Cat 1%, time: 25 min, yield 75%:

$^1$H NMR (400 MHz, CDCl$_3$) δ □=7.63 (s, 2H), 5.15 (s, 4H), 4.24 (q, J=7.3 Hz, 4H), 3.80 (q, J=7.1 Hz, 12H), 2.59 (br, 4H), 2.45 (m, 4H), 2.12 (br, 4H), 1.59 (m, 4H), 1.29 (t, J=7.4 Hz, 6H), 1.22 (t; J=7.1 Hz, 18H), 0.56 (m, 4H). $^{13}$C NMR (δ, ppm): 166.6; 124.3; 62.4; 58.5; 58.3; 57.6; 51.7; 50.9; 49.1; 20.6; 18.5; 14.2; 8.0.

EXAMPLE 3: PREPARATION OF A POLYSILYLATED ORGANOSILANE COMPOUND ACCORDING TO THE INVENTION

In a micro-wave reactor were introduced:

a compound of formula 15 (2.0 mmol)

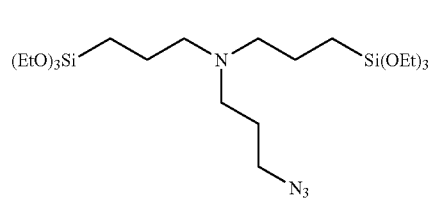

15 an organic alkyne (2.0 mmol of alkyne function) of formula

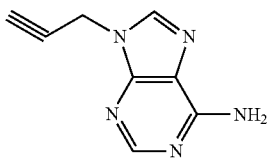

a catalyst [CuBr(PPh$_3$)$_3$],
in a 1:1 mixture THF/Et$_3$N (1 ml).

The mixture was irradiated at 100° C. for the indicated time, and then the volatile compounds were evaporated. After extraction with pentane (3×2 ml) and then concentration, the product 16 was obtained.

16

Cat 0.5%, time: 10 min, yield: 91%; solvent: DMF/Et$_3$N au lieu de THF/Et$_3$N.

$^1$H NMR (400 MHz, CDCl$_3$) δ=8.34 (s, 1H), 7.98 (s, 1H), 7.63 (s, 1H), 6.09 (s, 2H), 5.46 (s, 2H), 4.33 (t, J=7.3 Hz, 2H), 3.77 (q, J=7.0 Hz, 12H), 2.39 (t, J=8 Hz, 2H), 2.35 (t, J=8 Hz, 4H), 2.01-1.92 (m, 2H), 1.51-1.40 (m, 4H), 1.18 (t, J=7.0 Hz, 18H), 0.56-0.49 (m, 4H). $^{13}$C NMR (101 MHz, CDCl$_3$) δ=155.7, 153.1, 149.8, 142.2, 140.5, 123.1, 119.6, 58.4, 56.8, 50.7, 48.7, 36.7, 28.3, 20.2, 18.4, 8.0.

HRMS (ESI$^+$):

m/z calculated for C$_{29}$H$_{56}$N$_{90}$O$_6$Si$_2$: 682.3895;
m/z determined: 682.3895

EXAMPLE 4: PREPARATION OF A POLYSILYLATED ORGANOSILANE COMPOUND ACCORDING TO THE INVENTION

In a micro-wave reactor, were introduced:
a compound of formula 15 (2.0 mmol),

15

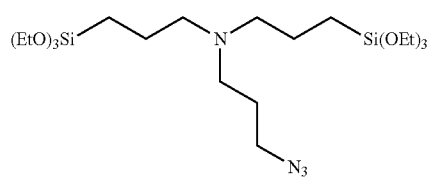

an organic alkyne (2.0 mmol of alkyne function) of formula

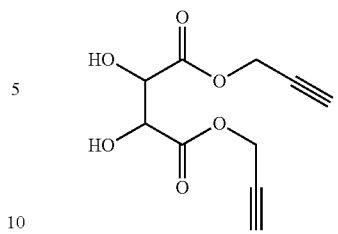

a catalyst [CuBr(PPh$_3$)$_3$],
in a 1:1 mixture THF/Et$_3$N (1 ml).

The mixture was irradiated at 100° C. for the indicated time, and then the volatile compounds were evaporated. After extraction with pentane (3×2 ml) and then concentration, the product 17 was obtained.

17

Cat 0.5%, time: 10 min, yield: 96%.

$^1$H NMR (400 MHz, CDCl$_3$) δ=7.35 (s, 2H), 5.09 (q, J=8.8 Hz, 2H), 4.30 (s, 2H), 4.11 (t, J=7.8 Hz, 4H), 3.52 (q, J=7.2 Hz, 24H), 2.41-2.25 (bs, 2H), 2.21-2.05 (m, 12H), 1.81-1.68 (m, 4H), 1.28-1.55 (m, 8H), 0.93 (t, J=7.2 Hz, 36H), 0.82-0.74 (m, 2H), 0.34-0.24 (m, 8H). $^{13}$C NMR (101 MHz, CDCl$_3$) δ=171.4, 142.0, 124.0, 67.3, 72.4, 58.5, 56.9, 50.7, 50.3, 28.4, 20.3, 18.5, 8.1.

HRMS (ESI$^+$):

m/z calculated for C$_{52}$H$_{107}$N$_8$O$_{18}$Si$_4$: 1243.6780;
m/z determined: 1243.6793

EXAMPLE 5: PREPARATION OF AN ORGANOSILICON MATERIAL WITH A PYRENE FUNCTION

A material of formula 18 was prepared with two different methods:

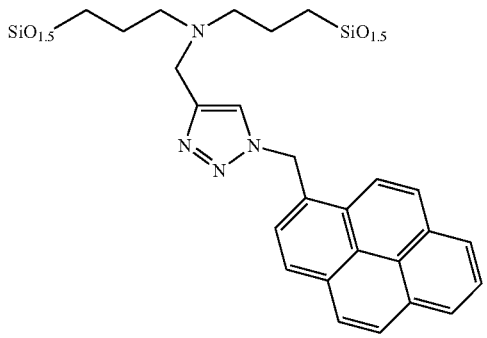

18

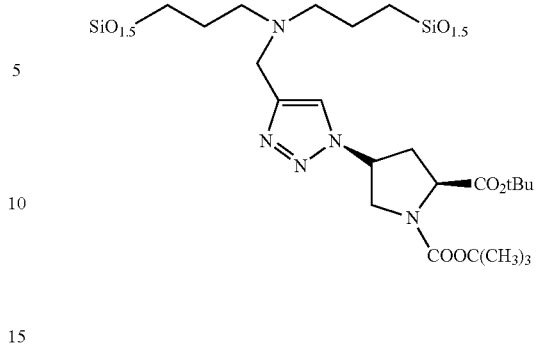

19

By Acid Catalysis

A mixture of compound 3 (5.7 mmol), of distilled water (122 ml, 6.8 mol) and of hydrochloric acid (12 M, 0.2 ml, 2.4 mmol), was vigorously stirred for one hour at 80° C. in a sealed tube, and then kept at rest at 80° C. for 48 hours.

The composition of the mixture was: compound 3/H$_2$O/ HCl=1:1200:0.4.

After cooling, the precipitate was spin-dried, successively washed with water, acetone and then ether, and dried under reduced pressure for 3 hours.

The thereby obtained product is characterized in the following way:

IR (wavenumbers in cm$^{-1}$): 706; 842; 1023; 1186; 1456; 1589; 2880; 2931; 3047.

$^{13}$C NMR CPMAS (δ, ppm): 146; 126; 62; 58; 22; 12.

$^{29}$Si NMR CPMAS (δ, ppm): −51 (T$^1$): −59 (T$^2$); −67 (T$^3$); Condensation rate: 90%

Elementary analysis: H, 4.5%; C, 52.5%; N, 8.9%.

By Nucleophilic Catalysis

A solution of tetrabutylammonium fluoride (1 M in THF, 0.10 ml, 0.10 mmol) and of distilled water (1.2 ml, 66 mmol) were added to a solution of compound 3 (5.6 mmol) in dry ethanol (20 ml).

The composition of the mixture was: compound 3/water/ TBAF=1:12:0.02.

The formation of a gel was observed after 20 minutes. After 48 hours under static conditions, the gel was crushed on a frit, and then successively washed with water, acetone and then ether, and finally dried under reduced pressure for 3 hours.

The thereby obtained product is characterized in the following way:

IR (wavenumbers in cm$^{-1}$): 706; 842; 1045; 1086; 1455; 1589; 2880; 2929; 2972; 3329.

$^{13}$C NMR CPMAS (δ, ppm): 146; 126; 62; 58; 52; 22; 19; 12.

$^{29}$Si NMR CPMAS (δ, ppm): −51 (T$^1$): −59 (T$^2$); −67 (T$^3$); Condensation rate: 81%.

Elementary analysis: H, 6.37%; C, 59.4%; N, 9.2%.

EXAMPLE 6: PREPARATION OF AN ORGANOSILICON MATERIAL WITH A PROLINE FUNCTION

A material of formula 19 was obtained with the following method:

A solution of tetrabutylammonium fluoride (1 M in THF, 0.10 ml, 0.10 mmol) and of distilled water (1.2 ml, 66 mmol) were added to a solution of compound 20 (5.6 mmol) in dry ethanol (20 ml).

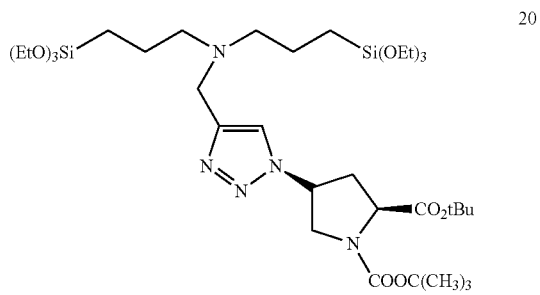

20

The composition of the mixture was: compound 20/water/ TBAF=1:12:0.02.

The formation of a gel was observed after 20 minutes. After 48 hours under static conditions, the gel was crushed on a frit, and then successively washed with water, acetone and then ether, and finally dried under reduced pressure for 3 hours.

The product thus obtained is characterized in the following way:

IR (wavenumbers in cm$^{-1}$): 718; 919; 1019; 1118; 1199; 1370; 1628; 1673; 1733; 2892; 2936.

$^{13}$C NMR CPMAS (δ, ppm): 173; 169; 138: 116; 84; 58; 42; 27; 19; 11

$^{29}$Si NMR CPMAS (δ, ppm): −51 (T$^1$): −59 (T$^2$); −67 (T$^3$); Condensation rate: 84%.

Elementary analysis: H, 5.2%; C, 32.3%; N, 10.9%.

EXAMPLE 7: PREPARATION OF AN ORGANOSILICON MATERIAL WITH PYRENE FUNCTIONS

A material of formula 21 was obtained with the following method:

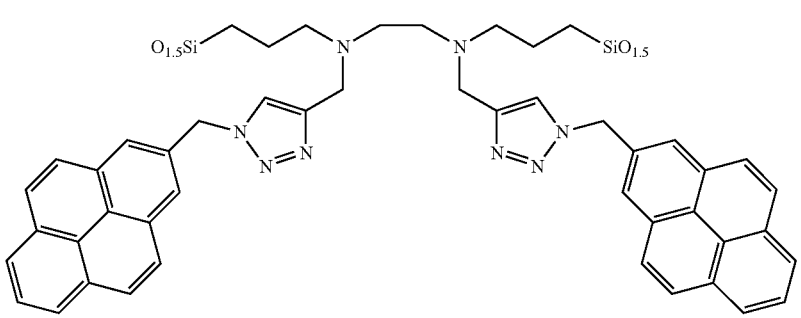

21

A mixture of compound (14) (1.0 mmol), of distilled water (20 ml, 1.2 mol) and of hydrochloric acid (1 M, 0.4 ml, 0.4 mmol) was vigorously stirred for 1 h at 80 C, and then left at rest at this temperature for 48 h. The precipitate was spin-dried, and successively washed with water, acetone and diethyl ether, and then dried in vacuo.

The thereby obtained product was characterized in the following way:

IR (wavenumber in cm$^{-1}$): 705; 758; 926; 1045; 1092; 1185; 1320; 1436; 1460; 1590; 1605; 2819; 2933; 3040; 3144.

$^{13}$C NMR CP-MAS (δ, ppm): 146; 126; 58; 52; 21; 12.

$^{29}$Si NMR CP-MAS (δ, ppm): −60 (T$^2$); −68 (T$^3$).

Condensation rate: 82%.

EXAMPLE 8: PREPARATION OF AN ORGANOSILICON MATERIAL WITH ETHYL ACETATE FUNCTIONS

A material of formula (23) was prepared with two different methods:

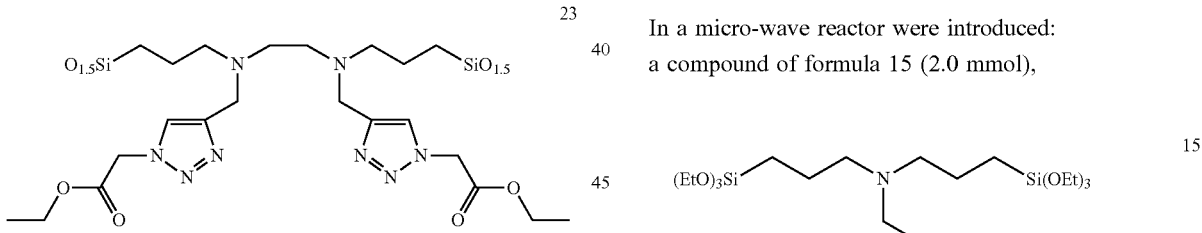

23

1—by Acid Catalysis

A mixture of compound (22) (4.5 mmol), of distilled water (20 mL, 1.1 mol) and of hydrochloric acid (1 M, 2.3 mL, 2.3 mmol) was vigorously stirred for 20 h at room temperature.

The composition of the mixture was 22/H$_2$O/HCl=1: 2500:5.

The solvent was evaporated for obtaining the material (23). The powder was washed with methanol and dried under reduced pressure at 40° C. for 6 hours.

The thereby obtained product was characterized in the following way:

IR (wavenumber in cm$^{-1}$): 095, 1018, 1055, 1091, 1215, 1344, 1376, 1467, 1736, 2949, 3140.

2—by Acid Catalysis in the Presence of a Surfactant

The compound (22) (0.42 mmol) was added to a mixture of SHS (sodium hexadecyl sulphate containing 40% by weight of sodium steararyl sulphate based on the total weight of the surfactant, 130 mg, 0.38 mmol), distilled water (20 ml, 1.1 mol) and HCl (1 M, 4 ml, 4 mmol) heated to 60° C.

The composition of the mixture was 22/SHS/HCl/H$_2$O=1: 0.9:9.5:3100

A white precipitate appears one minute later, the mixture is left with stirring for 20 hours at 50° C. and then filtered on a buchner. The extraction was accomplished by stirring the powder in basic ethanol (5 mL of NH$_4$OH 25% in 100 ml of ethanol) at 45° C. for 48 hours.

The thereby obtained product was characterized in the following way:

IR (wavenumber in cm$^{-1}$): 919, 1055, 1099, 1378, 1468; 1744, 2933, 3148.

EXAMPLE 9: PREPARATION OF A POLYSILYLATED ORGANOSILANE COMPOUND ACCORDING TO THE INVENTION

In a micro-wave reactor were introduced:

a compound of formula 15 (2.0 mmol),

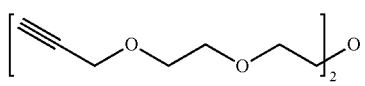

15 an organic alkyne (2.0 mmol of alkyne function) of formula a catalyst [CuBr(PPh$_3$)$_3$], in a 1:1 mixture THF/Et$_3$N (1 ml).

The mixture was irradiated at 100° C. for the indicated time, and then the volatile compounds were evaporated. After extraction with pentane (3×2 ml) and then concentration, the product 24 was obtained.

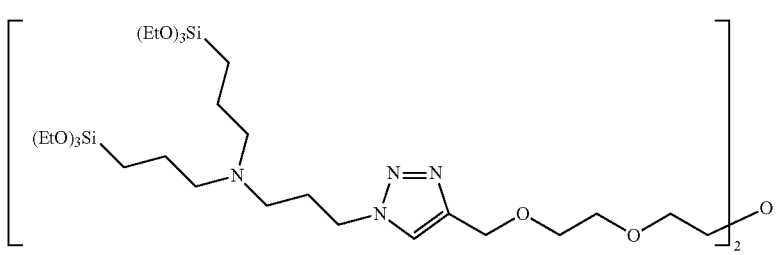
Cat 0.5%, time: 5 min, yield: 91%.
$^{1}$H NMR (400 MHz, CDCl$_3$) δ=7.55 (s, 2H), 4.67 (s, 4H), 4.38 (t, J=7.2 Hz, 4H), 3.81 (q, J=7.1 Hz, 24H), 3.69-3.60 (m, 16H), 2.45 (t, J=6.8 Hz, 4H), 2.40 (t, J=6.8 Hz, 8H), 2.02 (m, 4H), 1.50 (m, 8H), 1.22 (t, J=7.1 Hz, 36H), 0.57 (m, 8H).
$^{13}$C NMR (101 MHz, CDCl$_3$) δ=145.0, 122.7, 70.65 (2C), 70.60, 69.7, 64.7, 58.4, 56.9, 50.9, 48.6, 28.5, 20.3, 18.4, 8.1.
HRMS (ESI$^+$)
m/z calculated for C$_{56}$H$_{118}$N$_8$O$_{17}$Si$_4$, 1287.7770
m/z determined: 1287.7776
The invention claimed is:
1. A compound selected from the group consisting of the following formulas:
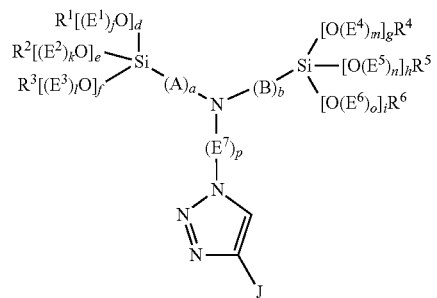
(IIe)
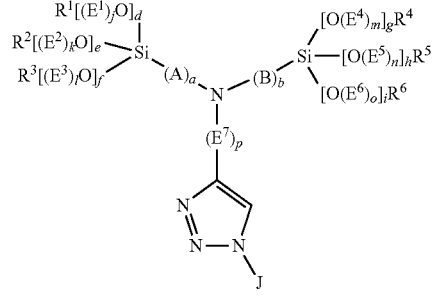
(IIf)
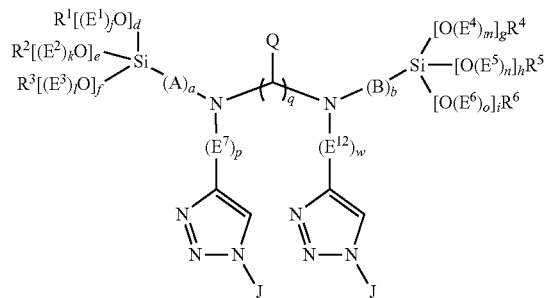
(IIh)
-continued
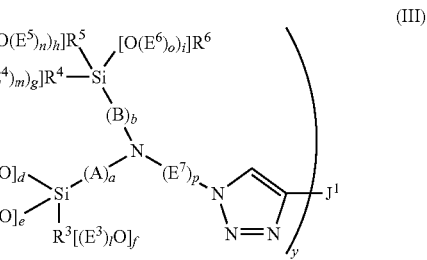
(III)
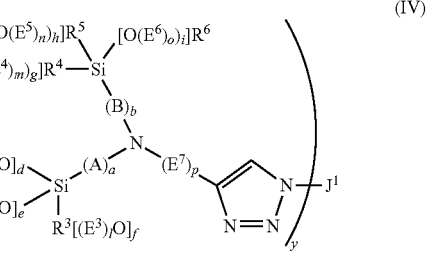
(IV)
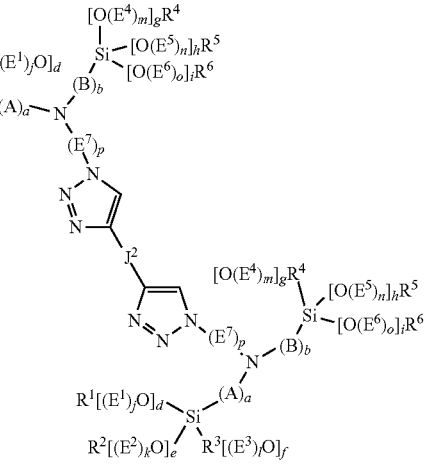
(IIIa)

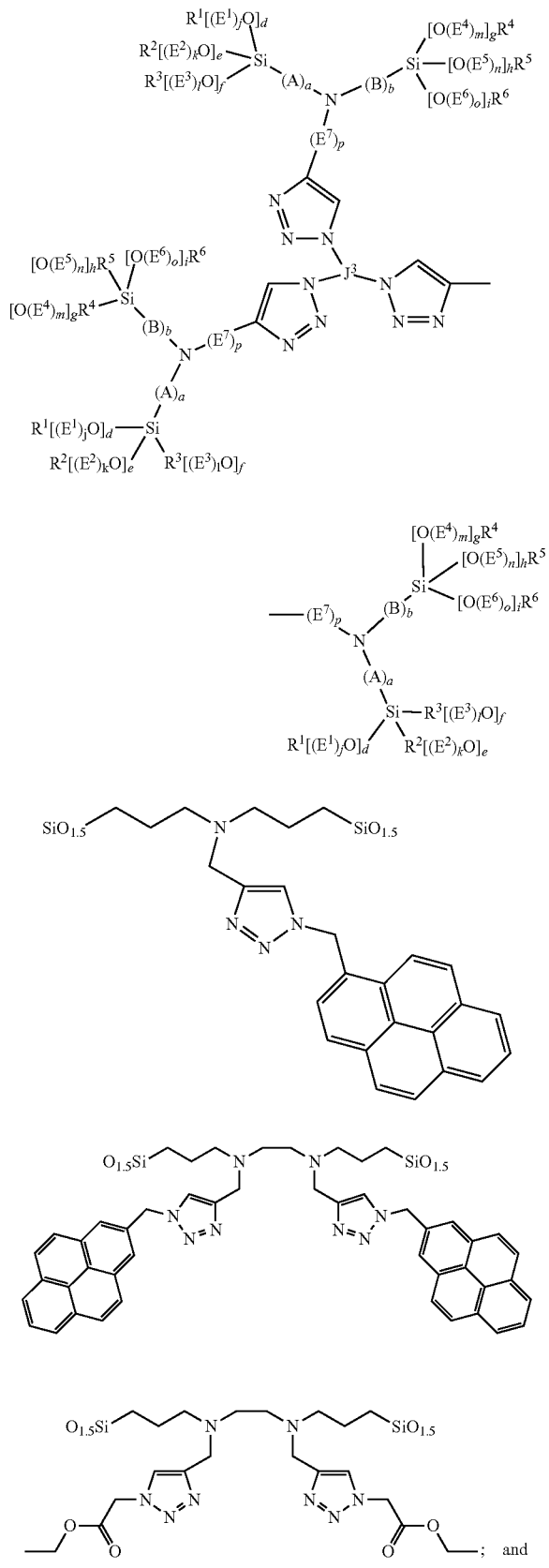

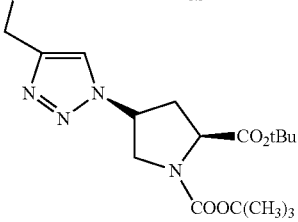

wherein:
- $R^1$, $R^2$, $R^3$, $R^4$, $R^5$ and $R^6$, either identical or different, represent a hydrogen atom, a $C_1$-$C_6$-alkyl group, an aryl group, a $C_1$-$C_6$-alkoxy group, a $C_3$-$C_8$-alkylene-alkenyl group;
- $E^1$, $E^2$, $E^3$, $E^4$, $E^5$ and $E^6$, either identical or different, represent a $C_1$-$C_6$-alkylene group, C(O), C=$CH_2$ group, an imino-$C_1$-$C_6$-alkyl group, a group ($C_1$-$C_6$-alkyl)C=N—;
- d, e, f, g, h, i, either identical or different, represent 0, 1, 2, 3, 4, 5, 6;
- j, k, l, m, n, o, either identical or different, represent 0, 1, 2, 3;
- a represents 1, 2, 3, 4, 5, 6, 7, 8, 9, 10, 11 or 12;
- B represents a group —$CR^{12}R^{13}$
- b represents 1, 2, 3, 4, 5, 6, 7, 8, 9, 10, 11 or 12;
- Q represents a hydrogen atom;
- q represents 0 or 2;
- $E^7$, and $E^{12}$ either identical or different, represent a group —$CR^{14}R^{15}$;
- $R^{10}$, $R^{11}$, $R^{12}$, $R^{13}$, $R^{14}$, and $R^{15}$, either identical or different, represent a hydrogen atom, a $C_1$-$C_6$-alkyl group, a $C_1$-$C_6$-alkoxy group, a $C_3$-$C_8$-alkylene-alkenyl group, an aryl group, or an aryloxy group;
- J represents a terminal atom or group, an atom or a divalent, trivalent, tetravalent, pentavalent or hexavalent, mono- or polyfunctional group;
- p and w, either identical or different, represent 1, 2, 3, 4, 5, 6, 7, 8, 9, 10, 11 or 12;
- $J^1$ represents an atom or a divalent, trivalent, tetravalent, pentavalent or hexavalent, mono- or poly-functional group;
- y represents 2, 3, 4, 5, 6;
- $J^2$ represents a divalent, mono- or poly-functional group;
- $J^3$ represents a trivalent, mono- or poly-functional group;
as well as an enantiomer, an isomer or a diastereoisomer of this compound.

2. The compound according to claim 1, wherein
A and B represents a group —($CH_2$)—; or
$R^1$, $R^2$, $R^3$, $R^4$, $R^5$ and $R^6$ represent independently a Me or Et group; or
a represents 1, 2 or 3; or
b represents 1, 2 or 3; or
d, e, f, g, h and i, either identical or different, represent 0 or 1; or
j, k, l, m, n and o represent 0.

3. The compound according to claim 1, wherein
A and B represent a group —($CH_2$)—;
Q represents a hydrogen atom;
$R^1$, $R^2$, $R^3$, $R^4$, $R^5$ and $R^6$ represent independently an Me or Et group;
a represents 1, 2 or 3;
b represents 1, 2 or 3;

d, e, f, g, h and i, either identical or different, represent 0 or 1;

j, k, l, m, n and o represent 0.

4. The compound according to claim 1 wherein:

A and B represents a group —(CH$_2$)—;

a represents 1, 2 or 3;

b represents 1, 2 or 3.

5. The compound according to claim 1, wherein J, J$^1$, J$^2$, and J$^3$ represent independently a mono- or poly-functional group comprising at least one functional group selected from the group consisting of a coloring group, a catalyst group, a group allowing molecular recognition, a biologically active group, a redox group, a hydrophilic group, a hydrophobic group, a decontaminating complexing group, a catalyst complexing group, and a cross-linking group.

6. The compound according to claim 1, wherein the functional group is selected from:
- a colouring group selected from an azoic, triphenylmethane, phthalein, a quinonic, an indigoid, an azinic, a porphyrin, a phthalocyanin, boron-dipyromethene, naphthalimide, polyaromatic, pyrene, acridine, and derivatives thereof, a colouring agent comprising a conjugate π system, a fluorescent colouring agent or a phosphorescent colouring agent;
- a catalyst group selected from a proline, a prolinamide, a diaryl-prolinol, 1, 1'-bis-2-naphthol, trans-1,2-diaminocyclohexane, tartaric acid, 1,2-diphenylethylenediamine, bisoxazoline, phosphine-oxazoline, pyridine-bisoxazoline, triarylphosphine, diphosphine, an imidazolium salt, a N-heterocyclic metal-carbene complex, a bipyridine, a pyridine, a phenanthroline, cyclopentadiene and derivatives thereof;
- a group allowing molecular recognition selected from a nitrogen-containing base, a melamine and derivatives thereof;
- a redox group selected from a metallocene, 1,4-(4-aminophenyl)-butadiene, a fullerene, a carbon nanotube and derivatives thereof;
- a hydrophobic group selected from a C$_1$-C$_{30}$ alkyl group, non-substituted or substituted with at least one fluorine atom, an aryl group;
- a decontaminating complexing group selected from an amine, an alcohol, a pyridine, a bipyridine, a triarylphosphine, a malonamide, a diacid, a diketone and derivatives thereof;
- a catalyst complexing group selected from a proline, a diarylprolinol and derivatives thereof;
- a cross-linking group selected from butadiene, butadiyn, an acrylate, a methacrylate, vinyl, styryl and derivatives thereof;
- a structuring group selected from a pyrrole, thiophene, alkylene or phenylene.

7. The compound according to claim 1 wherein J represents a mono- or poly-functional group comprising at least one functional group selected from:
- a colouring group selected from boron-dipyromethene, a naphthalimide, a porphyrin, a phthalocyanin, an azoic, an indigoid, a phthalein, a quinonic and derivatives thereof;
- a decontaminating complexing group selected from an amine, an alcohol, a pyridine, a triarylphosphine, a malonamide, a diacid, a diketone and derivatives thereof;
- a group allowing molecular recognition selected from a nitrogen-containing base, a melamine and derivatives thereof;
- a catalyst complexing group selected from a proline, a diarylprolinol and derivatives thereof;
- a redox group selected from a metallocene;
- a hydrophobic group selected from a C$_1$-C$_{30}$ alkyl group, non-substituted or substituted with at least one fluorine atom;
- a structuring group selected from a pyrrole or a thiophene.

8. The compound according to claim 1 wherein J$^2$ represents a mono- or poly-functional group comprising at least one functional group selected from:
- a colouring group selected from boron-dipyromethene, a porphyrin, a phthalocyanin, an azoic, an indigoid, a phthaleine, a quinonic, triphenylmethane, a colouring agent comprising at least a conjugate π system, a pyrene and derivatives thereof;
- a decontaminating complexing group selected from a pyridine, a bipyridine, a triarylphosphine, a malonamide, a diketone and derivatives thereof;
- a group allowing molecular recognition selected from a melamine and derivatives thereof;
- a catalyst group selected from a binol, a derivative of 2,2'-bis(diphenylphosphino)-1,1'-binaphthyl (BINAP), a derivative of 2,2'-diamino-1,1'-binaphthyl (BINAM), trans-1,2-diaminocyclohexane, 1,2-diphenylethylene-1,2-diamine, tartaric acid and derivatives thereof;
- a redox group selected from 1,4-(4-aminophenyl)-butadiene, a metallocene and derivatives thereof;
- a hydrophobic group selected from a C$_1$-C$_{30}$ alkyl group, non-substituted or substituted with at least one fluorine atom, an aryl group;
- a structuring group selected from a thiophene, an alkylene.

9. The compound according to claim 1 wherein J$^3$ represents a mono- or poly-functional group comprising at least one functional group selected from:
- a decontaminating complexing group selected from a triarylphosphine and derivatives thereof,
- a group allowing molecular recognition selected from a melamine and derivatives thereof,
- a structuring group such as a phenylene.

\* \* \* \* \*